United States Patent
Bauta et al.

(10) Patent No.: US 10,576,077 B2
(45) Date of Patent: Mar. 3, 2020

(54) PHARMACEUTICAL SALT FORMS OF CEPHARANTHINE AND TETRANDRINE

(71) Applicant: Southwest Research Institute, San Antonio, TX (US)

(72) Inventors: William E. Bauta, San Antonio, TX (US); Joseph A. McDonough, Helotes, TX (US); Hong Dixon, Helotes, TX (US); Stephen T. Wellinghoff, San Antonio, TX (US); Kevin Fitzpatrick, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 15/925,551

(22) Filed: Mar. 19, 2018

(65) Prior Publication Data

US 2018/0303823 A1    Oct. 25, 2018

Related U.S. Application Data

(63) Continuation-in-part of application No. 15/078,782, filed on Mar. 23, 2016, now abandoned.

(60) Provisional application No. 62/136,851, filed on Mar. 23, 2015.

(51) Int. Cl.
*A61K 31/4745* (2006.01)
*A61K 9/16* (2006.01)
*C07D 491/22* (2006.01)

(52) U.S. Cl.
CPC ........ *A61K 31/4745* (2013.01); *A61K 9/1635* (2013.01); *C07D 491/22* (2013.01); *A61K 9/1682* (2013.01)

(58) Field of Classification Search
CPC ............................ A61K 31/4745; A61K 31/47
See application file for complete search history.

(56) References Cited

U.S. PATENT DOCUMENTS

| | | | |
|---|---|---|---|
| 2,248,241 A * | 7/1941 | Kondo | C07D 491/18 546/31 |
| 4,816,462 A | 3/1989 | Nowicky | |
| 5,534,523 A | 7/1996 | Ono et al. | |
| 6,123,943 A | 9/2000 | Baba et al. | |
| 6,562,837 B1 | 5/2003 | Yun-Choi et al. | |
| 8,067,401 B2 | 11/2011 | Chepkwony et al. | |
| 8,475,804 B2 | 7/2013 | Johansen et al. | |
| 8,889,743 B2 | 11/2014 | Davey et al. | |
| 9,517,234 B2 | 12/2016 | Carroll | |
| 9,518,022 B2 | 12/2016 | Atuegbu et al. | |
| 2011/0028564 A1 | 2/2011 | Johansen et al. | |
| 2011/0152344 A1 | 6/2011 | Davey et al. | |
| 2014/0073591 A1 | 3/2014 | Gudeman et al. | |
| 2014/0275137 A1 | 9/2014 | Carroll | |
| 2016/0280716 A1 | 9/2016 | Bauta et al. | |
| 2017/0368051 A1 | 12/2017 | Atuegbu et al. | |

FOREIGN PATENT DOCUMENTS

| | | | |
|---|---|---|---|
| CN | 102477041 A * | 5/2012 | |
| CN | 102477041 A | 5/2012 | |
| EP | 0 476 391 A2 | 3/1992 | |
| EP | 0476391 A2 * | 3/1992 | ............. A61K 31/47 |
| EP | 1 124 554 A2 | 9/2003 | |
| JP | 2000080039 A | 3/2000 | |
| KR | 10 0352425 B1 | 9/2002 | |
| WO | 2014149848 A1 | 9/2014 | |

OTHER PUBLICATIONS

Vippagunta et al (Crystalline Solids: Advanced Drug Delivery Reviews vol. 48 pp. 3-26 published 2001 (Year: 2001).*
Speakman Basics of X-Ray Powder Diffraction X-Ray training materials at MIT. Accessed Mar. 18, 2014 (Year: 2014).*
Brittain et al. "Polymorphism in Pharmaceutical Dosage Forms." Polymorphism in Pharmaceutical Solids XX (Jan. 1999) pp. 235-238 (Year: 1999).*
U.S. Office Action dated Sep. 14, 2018; issued in related U.S. Appl. No. 15/916,596 (8 pgs).
Ashtikar, et al, "Transdermal Delivery from Liposomal Formulations—Evolution of the Technology Over the Last Three Decades", Science Direct; Journal of Controlled Release, vol. 242, pp. 126-140; published online Sep. 10, 2016.
Bhattacharya, et al; "Polymorphism in Pharmaceutical Solids, Second Edition"; Chapt. 9 "Thermoanalytical and Crystallographic Methods" (Jan. 1999), Informa Healthcare USA, RightsLinkpp. 318-346 downloaded by USPTO on Oct. 20, 2014.
Chen, et al, "The Alkaloids of Han-Fang-Chi", from the Lilly Research Laboratories, received for publication Mar. 7, 1935, pp. 681-685.
Goho; "Tricky Business—The Crystal Form of a Drug Can be the Secret to its Success"; Science News Online; week of Aug. 21, 2004; vol. 166, No. 8; (8 pgs) <<http://www.sciencenews.org/scripts/printthis.asp?clip-%2Farticles%2F20040821%2Fclip>> accessed Feb. 28, 2005.
Hussan, et al; "A Review on Recent Advances of Enteric Coating"; IOSR Journal of Pharmacy, vol. 2, Issue 6, Nov.-Dec. 2012; pp. 5-11.
Inubushi, et al; "Total Syntheses of Optically Active Natural Isotetrandrine, Phaeanthine and Tetrandrine", Tetrahedron Letters No. 30, pp. 3399, 1968 Pergamon Press; Great Britain.

(Continued)

*Primary Examiner* — Timothy P Thomas
*Assistant Examiner* — George W Kosturko
(74) *Attorney, Agent, or Firm* — Grossman, Tucker, Perreault & Pfleger, PLLC

(57) ABSTRACT

The present disclosure relates to the preparation of polymorphic mixtures of Cepharanthine.2HCl. Mixtures of at least two polymorphic forms can be formed into a mobile liquid phase in organic/aqueous solvent mixtures along with enteric polymer that can be spray dried to produce solid particulate enteric formulations for medicinal drug-treatment applications.

Figure 1:
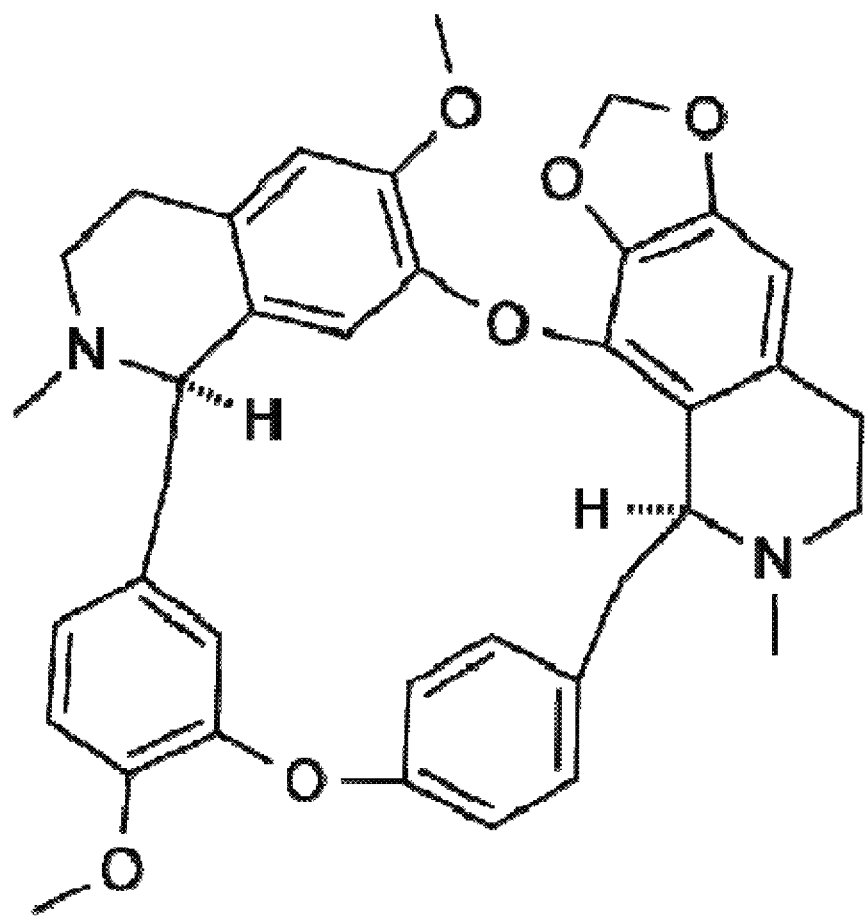
Figure 2:
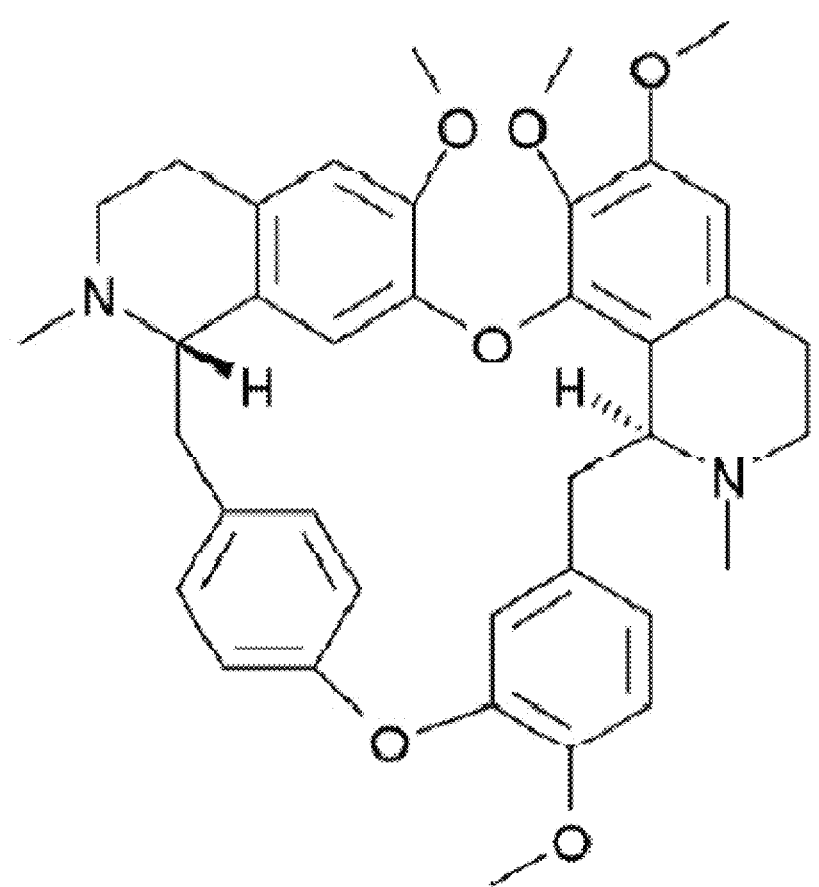

6 Claims, 27 Drawing Sheets
(7 of 27 Drawing Sheet(s) Filed in Color)

(56) References Cited

OTHER PUBLICATIONS

Jia, et al, "Local Application of Statins Significantly Reduced Hypertrophic Scarring in a Rabbit Ear Model", International Open Access Journal of the American Society of Plastic Surgeons; Plast Reconstr Surg Global Open, published online Jun. 14, 2017.
Kang, et al; "CaV1.3-Selective L-type Calcium Channel Antagonists as Potential New Therapeutics for Parkinson's Disease", Nature Communications 3, Article No. 1146, Oct. 23, 2012 (23 pgs).
Naylor, et al; "Identification of a Chemical Probe for NAADP by Virtual Screening"; Nat. Chem. Biol. Apr. 2009 5(4): 220-226; 18 pgs.
Price; "Polymorphism in Pharmaceutical Solids, Second Edition"; Chapt 3 "Computational Methodologies: Toward Crystal Structure and Polymorph Prediction"; Informa Healthcare USA, RightsLink, pp. 52-75 downloaded by USPTO on Oct. 20, 2014.
Stahl, et al; "Handbook of Pharmaceutical Salts: Properties, Selection and Use", 2nd Revised Edition, Abstract only; 3 pgs; Wiley-VCG, Apr. 2011.
Tsuji, et al; "New Finding of Glassy Liquid Crystal—a Non-equilibrium State of Cholesteryl Hydrogen Phthalate"; Short Ccommunications, vol. 44, No. 5, pp. 1452, Mar. 25, 1971.
Vippagunta, et al., "Crystalline Solids", Advanced Drug Delivery Reviews, vol. 48, published 2001, pp. 3-26.

\* cited by examiner

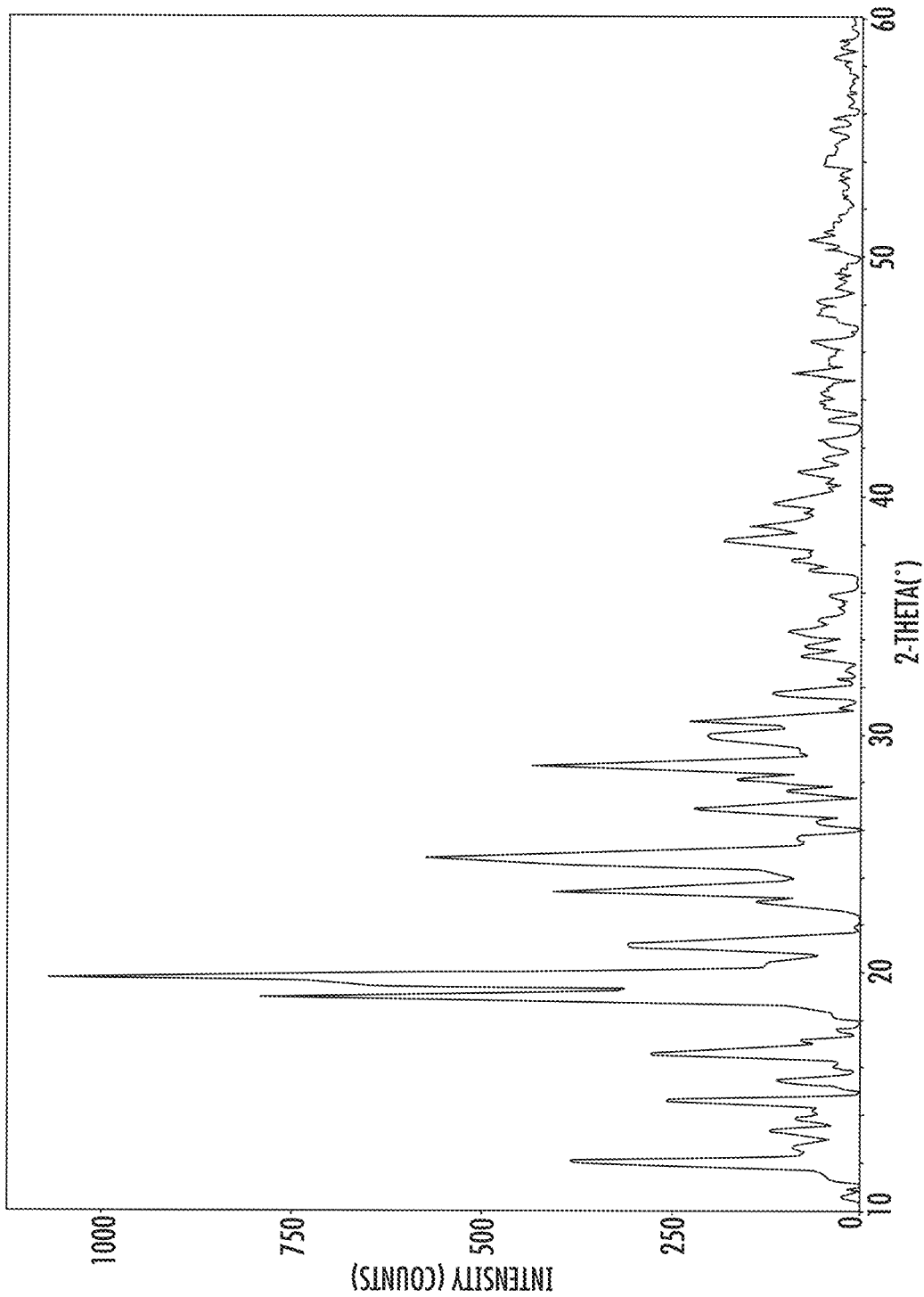

PHARMACEUTICAL SALT FORMS OF CEPHARANTHINE AND TETRANDRINE

CROSS REFERENCE TO RELATED APPLICATIONS

The application is a continuation-in-part of U.S. application Ser. No. 15/078,782, filed Mar. 23, 2016, which claims the benefit of the filing date of U.S. Provisional Application Ser. No. 62/136,851, filed Mar. 23, 2015, the teachings of which are incorporated herein by reference.

FIELD OF THE INVENTION

The present disclosure relates to the preparation of pharmaceutically acceptable salt forms of the medicinal alkaloids Cepharanthine and Tetrandrine with improved solubility and physicochemical properties compared with the free base form of these alkaloids. The disclosure includes the application of these salt forms to the treatment of diseases including viral infections, hypertension, cancer, neutropenia and, in a narrower embodiment, filovirus infections such as those resulting from Ebola and Marburg viruses and subtypes thereof.

BACKGROUND

There are currently no effective therapies for the treatment of filovirus infections such as those caused by Ebolavirus. Recent work has revealed that medicinal alkaloids from members of the botanical family *Stephania* can effectively treat and prophylactically protect against infection by Ebolavirus based on in vitro and in vivo experimental results. These alkaloids have been used extensively in Asia for a variety of ailments ranging from hypertension to cancer for many years and have been dosed orally. However, the very limited solubility (≤1 mg/mL) of these alkaloids in their free base forms is an impediment to their development as oral therapeutics or via alternative routes of administration such as IV (intravascular administration), IP (intraperitoneal injection) or IM (intramuscular injection).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above-mentioned and other features of this disclosure, and the manner of attaining them, will become more apparent and better understood by reference to the following description of embodiments described herein taken in conjunction with the accompanying drawings, wherein:

FIG. 1 illustrates Cepharanthine (CEPN);

FIG. 2 illustrates Tetrandrine (TETN);

FIG. 3A illustrates PXRD data for the Cepharanthine 2 HBr salt;

FIG. 3B illustrates the general structure of the Cepharanthine 2HBr salt.

FIG. 4A illustrates the Powder X-Ray Diffraction for Cepharanthine 2HCl salt;

FIG. 4B illustrates the Cepharanthine 2HCl salt.

FIG. 5 illustrates the DSC thermogram for the Cepharanthine 2HCl salt;

FIG. 6 illustrates the Powder X-Ray Diffraction data for the Cepharanthine 2HCl salt recovered from ethyl acetate;

FIG. 7 illustrates the Powder X-Ray Diffraction data for the Cepharanthine 2HBr salt recovered from ethanol-water;

FIG. 8 illustrates the DSC thermograph for Cepharanthine 2HBr;

FIG. 9 illustrates the Powder X-Ray Diffraction data for Cepharanthine 2HBr recovered from ethyl acetate;

FIG. 10 illustrates the Powder X-Ray Diffraction data for Cepharanthine 2Pyruvic acid;

FIG. 11 illustrates the DSC thermograph for Cepharanthine 2Pyruvic acid;

FIG. 12 illustrates the Powder X-Ray Diffraction data for three (3) Cepharanthine 2HCl samples noted in Table 3;

FIG. 13 illustrates the DSC thermograph for sample 1 of Table 3;

FIG. 14 illustrates the DSC thermograph for sample 2 of Table 3; and

FIG. 15 illustrates the DSC thermograph of sample 3 of Table 3.

FIG. 16A illustrates the x-ray powder diffraction patterns of the polymer distribution for CEPN Lab Production.

FIG. 16B illustrates the x-ray powder diffraction patterns of the polymer distribution for CEPN reference standard.

FIG. 16C illustrates the x-ray powder diffraction patterns of the polymer distribution for a 5 kg Engineering production.

FIG. 16D illustrates the x-ray powder diffraction patterns of the polymorph distribution for a 10 kg cGMP production.

FIG. 17A illustrates a polarized optical microscope image of CEPN 2HCl (13% w/w) in water starting with solids of different polymorph compositions (see Table 8).

FIG. 17B illustrates a polarized optical microscope image of CEPN 2HCl (13% w/w) in water starting with solids of different polymorph compositions (see Table 8).

FIG. 17C illustrates a polarized optical microscope image of CEPN 2HCl (13% w/w) in water starting with solids of different polymorph compositions (see Table 8).

FIG. 17D illustrates a polarized optical microscope image of CEPN 2HCl (13% w/w) in water starting with solids of different polymorph compositions (see Table 8).

FIG. 18 illustrates the strategy of enteric formulation of the CEPN 2HCl polymorphic mixtures herein.

FIG. 19 illustrates the preferred particle size distribution from spray drying and formation for the enteric formulations.

FIG. 20A provides polarized optical microscope images of the enteric.

FIG. 20B provides polarized optical microscope images of CEPN 2HCl crystals.

FIG. 21A contains the powder x-ray diffraction patterns of one of three enteric formulations of the polymorphic mixtures herein showing the amorphous structure of the composite.

FIG. 21B contains the powder x-ray diffraction patterns of one of three enteric formulations of the polymorphic mixtures herein showing the amorphous structure of the composite.

FIG. 21C contains the powder x-ray diffraction patterns of one of three enteric formulations of the polymorphic mixtures herein showing the amorphous structure of the composite.

FIG. 22A illustrates CEPN rat plasma concentration for oral (gavage) enteric does (25% w/w CEPN 2HCl in L100) of 50 mg/kg (rat weight) API.

FIG. 22B illustrates CEPN rat plasma concentration for oral (gavage) enteric does (25% w/w CEPN 2HCl in L100) of 150 mg/kg (rat weight) API.

Figure 22A:
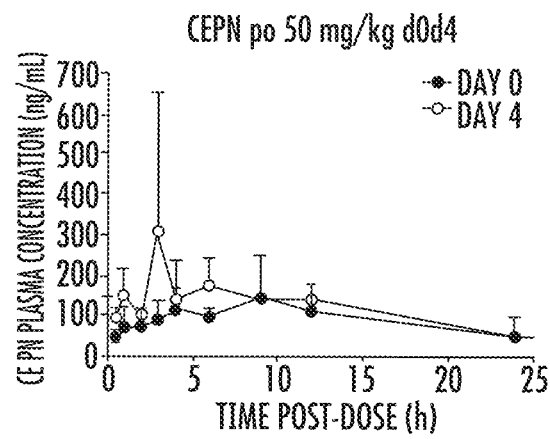
Figure 22B:
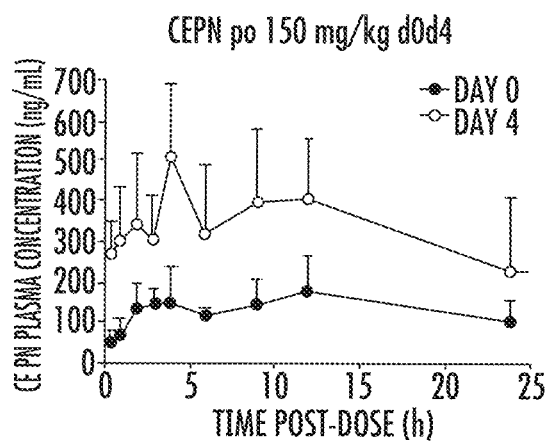
Figure 22C:
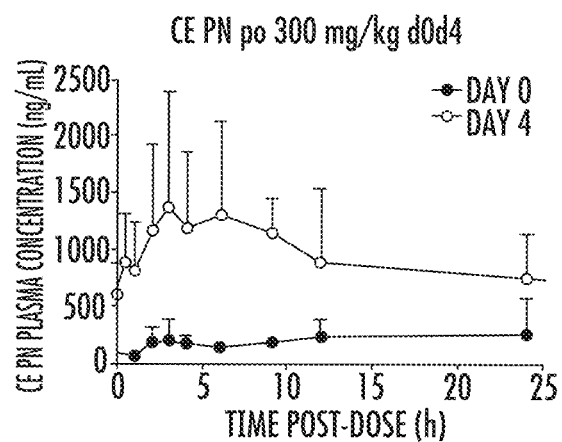

FIG. 22C illustrates CEPN rat plasma concentration for oral (gavage) enteric does (25% w/w CEPN 2HCl in L100) of 300 mg/kg (rat weight) API.

SUMMARY

A method of forming an enteric formulation of Cepharanthine.2HCl comprising:

(a) supplying the dihydrochloride salt of Cepharanthine comprising Cepharanthine.2 HCl of the following formula:

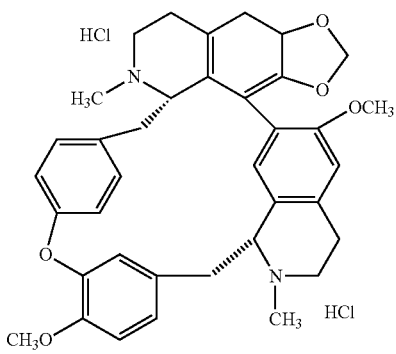

(b) recrystallizing said Cepharanthine.2HCl salt and forming a mixture of at least two polymorphs at a purity of ≥99.4%;

(c) introducing said recrystallized Cepharanthine.2HCl in combination with a polymer into a mixture of a water soluble organic solvent containing water to provide a liquid mobile phase;

(c) forming a solid enteric formulation from said liquid mobile phase to produce an enteric particle containing an amorphous liquid crystal form of said Cepharanthine.2HCl salt.

In addition, the present invention also relates to: (1) an enteric formulation comprising an amorphous liquid crystalline form of Cepharanthine.2HCl; and (2) a method for treating an individual with said formulation who has been exposed to or infected with a filovirus.

DETAILED DESCRIPTION

Pharmaceutically acceptable salt forms of CEPN and TETN, preferably of desired polymorphic forms, are prepared herein having superior solubility compared to the parent alkaloids and are applicable for the treatment of filovirus infection. It is contemplated herein that the pharmaceutically acceptable salts of the desired polymorphic forms will include various salts that may be sourced from either inorganic or organic type acids. Table 1 below identifies the contemplated inorganic and organic acids that may be employed.

TABLE 1

Pharmaceutically Acceptable Salt Forms of CEPN and TETN

| Inorganic acids | Organic Acids | | |
|---|---|---|---|
| Hydrochloric | Formic | Maleic | Benzoic |
| Hydrobromic | Acetic | Malonic | Glucoronic |
| Phosphoric | Methanesulfonic | Glutamic | Fumaric |
| Sulfuric | Tosic | Aspartic | |

TABLE 1-continued

Pharmaceutically Acceptable Salt Forms of CEPN and TETN

| Inorganic acids | Organic Acids | |
|---|---|---|
| Nitric | Tartaric | Pyruvic |
| | Lactic | Mucic |

The pharmaceutically acceptable salt forms of the desired polymorphic form were prepared by adding a suitable acid from the list in Table 1 to a solution of an alkaloid and isolation of the resultant salt either by crystallization or solvent evaporation protocol to promote formation of the desired polymorph. In preferred embodiments the salt form may include either the mono- or the bis-salt and this may be further purified by recrystallization from a suitable solvent.

A representative sample preparation procedure follows with respect to CEPN. Both tertiary amine groups in the alkaloid CEPN are contacted with the selected acid in an appropriate solvent system. All reactions were carried out in ambient temperature and pressure. The acids selected for the final salt formulations were etheric HCl and liquid methanesulfonic (MSA) and pyruvic acids, all of which were monobasic. Thus, exact Cepharanthine:acid molar ratio of 1:2 was used in all preparations. Ethanol was preferred as the common solvent in all preparations, except for that of MSA salt to avoid the known neurotoxic ester formation of MSA with alcohols. In that instance, dichloromethane (DCM) was used as the alternative solvent since Cepharanthine is well soluble in DCM.

The process for the preparation of pyruvic acid salt was accomplished as follows. Pure Cepharanthine (1.82 g, 3.0 mmol) was completely dissolved in ethanol (25 mL) and 2 equivalents of pyruvic acid (0.53 g, 6 mmol) in ethanol was added slowly while stirring. Additional ethanol was used to complete the pyruvic acid transfer. The mixture was stirred further 30 min before ethanol was evaporated in reduced pressure. The gummy residue was dissolved again in dichloromethane (DCM) and evaporated to obtain a foamy solid. Thus, the purification was completed by precipitation using DCM/heptanes solvent system followed by filtration of the solid, washing the solid with a mixture of solvent systems containing 2-propanol, DCM, and heptanes, and drying the solid under vacuum to obtain partially shiny solid (2.14 g, 91% yield). Comparison of $^1$H NMR spectra of both salt and Cepharanthine confirmed the formation of pyruvic acid salt.

The solubility of the salts prepared herein are identified below in Table 2.

TABLE 2

Solubility of Cepharanthine Salts in Water

| Sample ID | Description | Dilution needed | Final Concentration (mg/mL) |
|---|---|---|---|
| 1 | HCl salt | 1000x | 51.6 |
| 2 | HCl salt (diluted) | 1000x | 21.1 |
| 3 | HBr salt | 1000x | 17.1 |
| 4 | Benzoic Acid salt | 100x | 7.78 |
| 5 | Lactic Acid salt | 1000x | 41.2 |
| 6 | MSA salt | 20,000x | 800 |
| 7 | Pyruvic acid salt | 10,000x | 488 |

As can be seen from the above, preparation of pharmaceutically acceptable salts according to a preparation protocol that is contemplated to produce a particular resulting polymorphic salt structure is such that remarkably improved solubility is achieved which will then translate into more efficient drug delivery for treatment of filovirus infections.

Such polymorphic structure may also be readily confirmed by other analytical techniques, including but not limited to x-ray diffraction and identification of relative intensity counts and/or scanning electron micrographs which identifies variables such as the aspect ratio or range of aspect ratios that may be present.

Figure 3B:
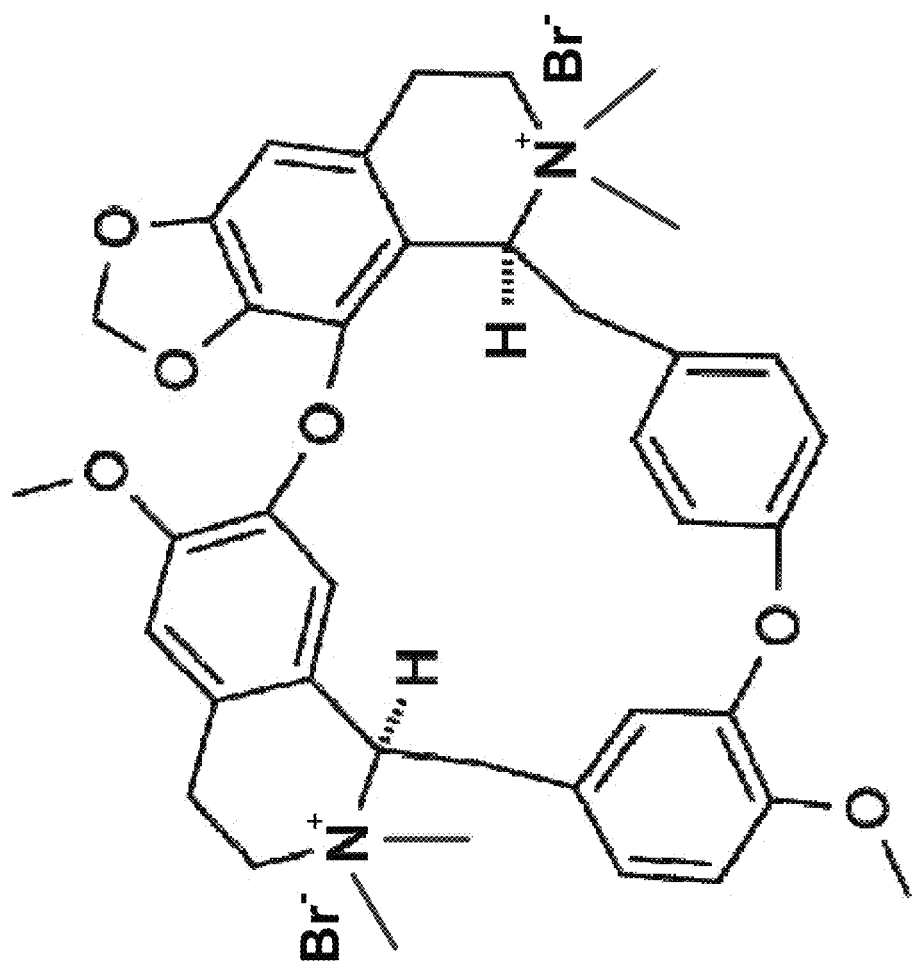

The process for the preparation of salt derivatives of Cepharanthine using various organic and inorganic acids can proceed as follows: the process comprises contacting both tertiary amine groups in the alkaloid Cepharanthine with the selected acid in an appropriate solvent system. All reactions were carried out in ambient temperature and pressure. The inorganic acids selected for the final salt formulations were HCl and HBr, which were obtained in either case as 2M solutions. The inorganic acids selected were methanesulfonic acid (MSA) and pyruvic acid, both of which were liquids. Since all of these acids were monobasic, the Cepharanthine to acid mole ratio of 1:2 was used in all salt preparations. Ethanol was preferred as the common solvent in all preparations, except for that of MSA salt to avoid the known neurotoxic ester formation of MSA with alcohols. In that instance, dichloromethane (DCM) was used as the alternative solvent since Cepharanthine is well soluble in DCM. FIG. 3A illustrates Powder X-Ray Diffraction (PXRD) data for the Cepharanthine 2HBr salt recovered from isopropanol. As can be seen, the PXRD indicates that a plurality of distinguishing x-ray diffraction peaks at 2 Theta angles of 10-35 degrees as compared to non-distinguishing x-ray diffraction peaks at 2 Theta angles of greater than 35 degrees, wherein said distinguishing x-ray diffraction peaks have relative intensity counts between 250-1250 at 2 Theta angles of 10-35 degrees and non-distinguishing x-ray diffraction peaks have relative intensity counts of less than 250 at 2 Theta angles of greater than 35 degrees. FIG. 3B illustrates the general structure of the Cepharanthine 2HCl salt.

Figure 4A:
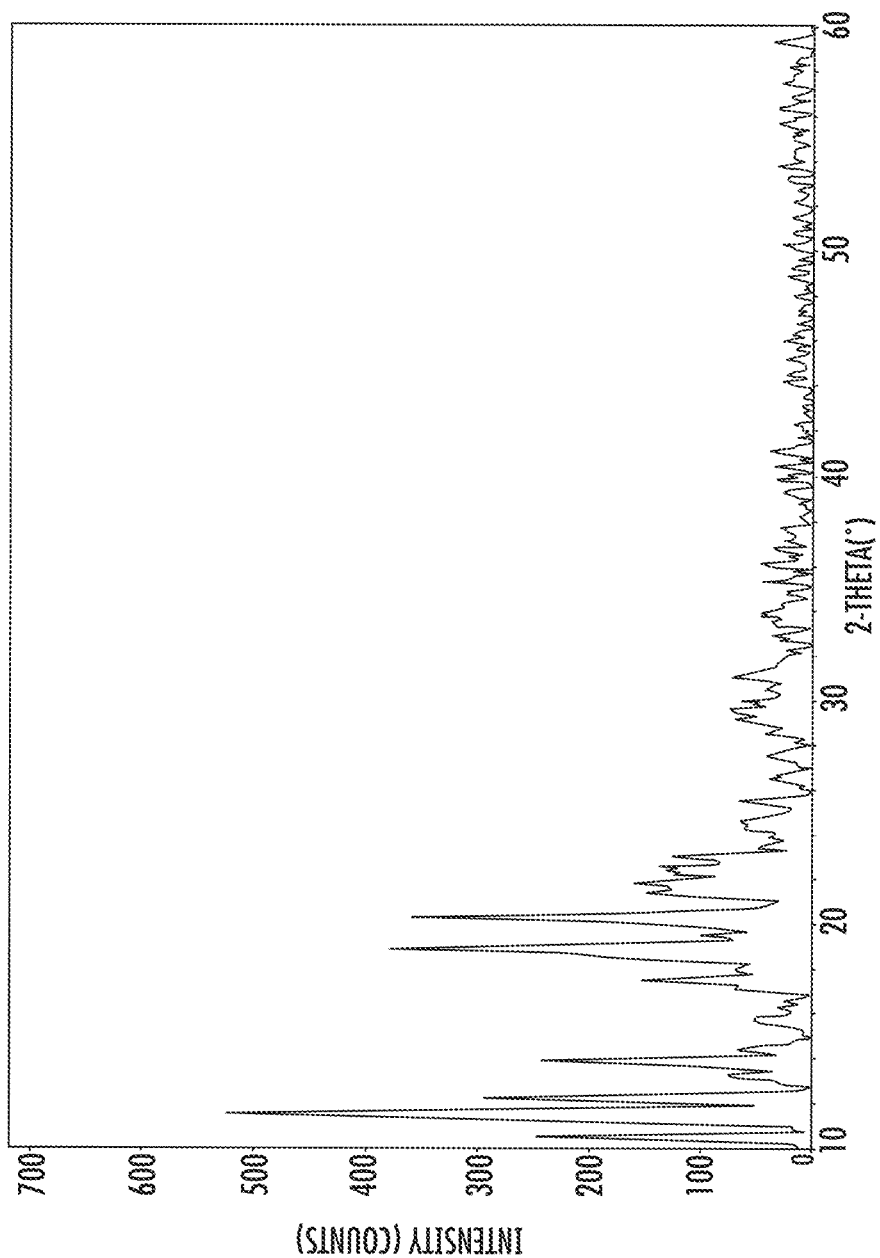
Figure 4B:
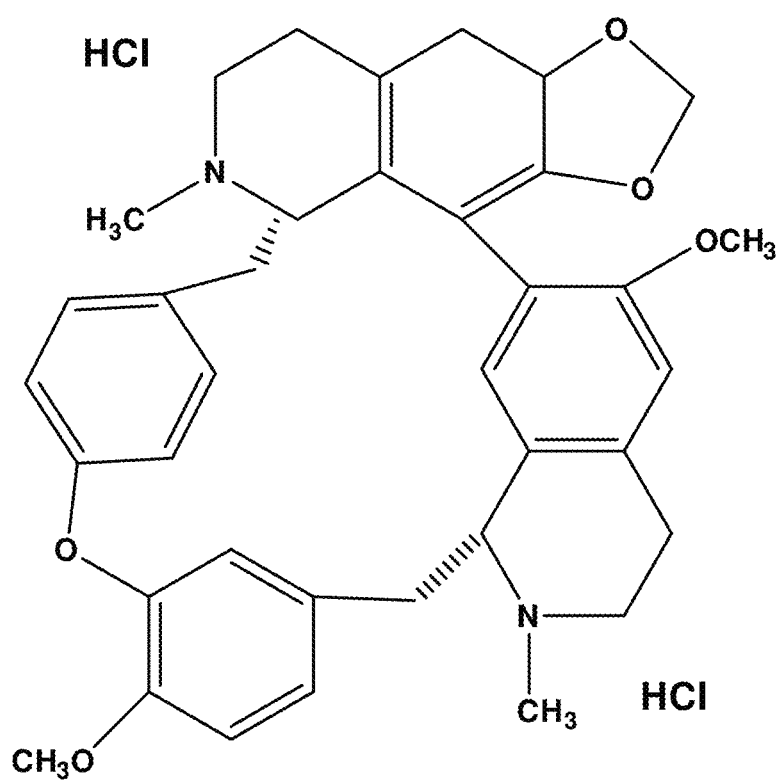

FIG. 4A illustrates the Powder X-Ray Diffraction (PXRD) for the Cepharanthine 2HCl salt. FIG. 4B illustrates the general structure of such salt. As can be seen, the PXRD indicates that a plurality of distinguishing x-ray diffraction peaks at 2 Theta angles of 10-25 degrees as compared to non-distinguishing x-ray diffraction peaks at 2 Theta angles of greater than 25 degrees, wherein said distinguishing x-ray diffraction peaks have relative intensity counts between 200-550 at 2 Theta angles of 10-25 degrees and non-distinguishing x-ray diffraction peaks have relative intensity counts of less than 100 at 2 Theta angles of greater than 35 degrees.

Figure 5:
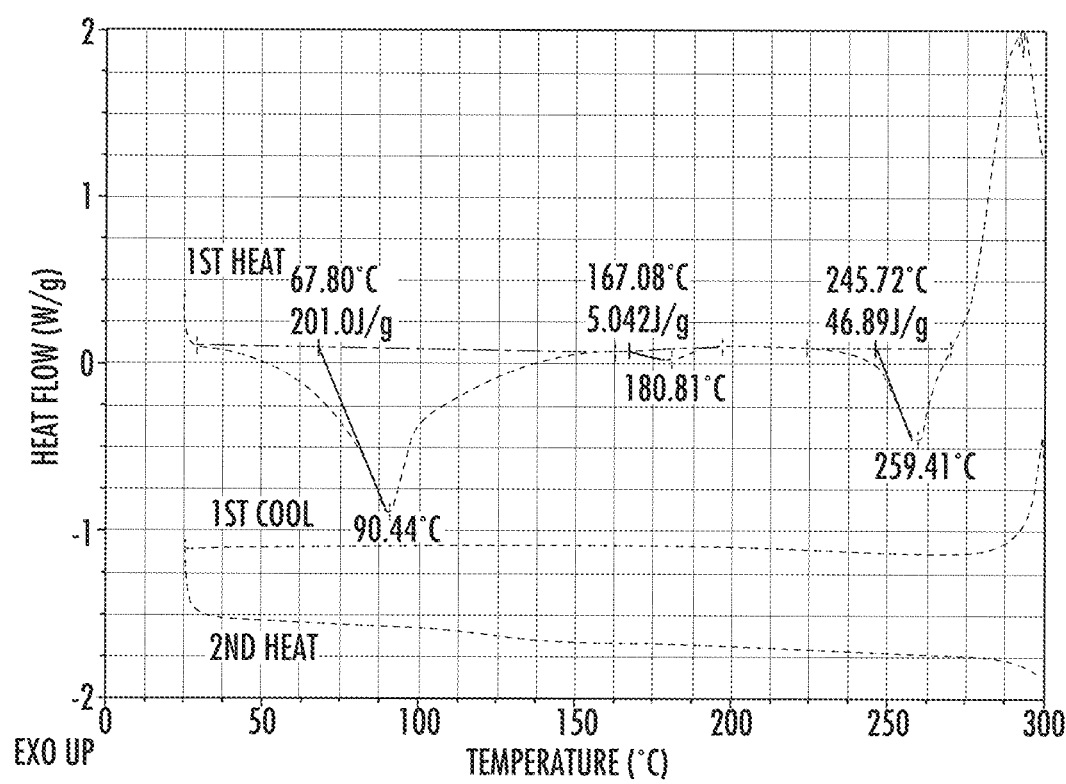
Figure 6:
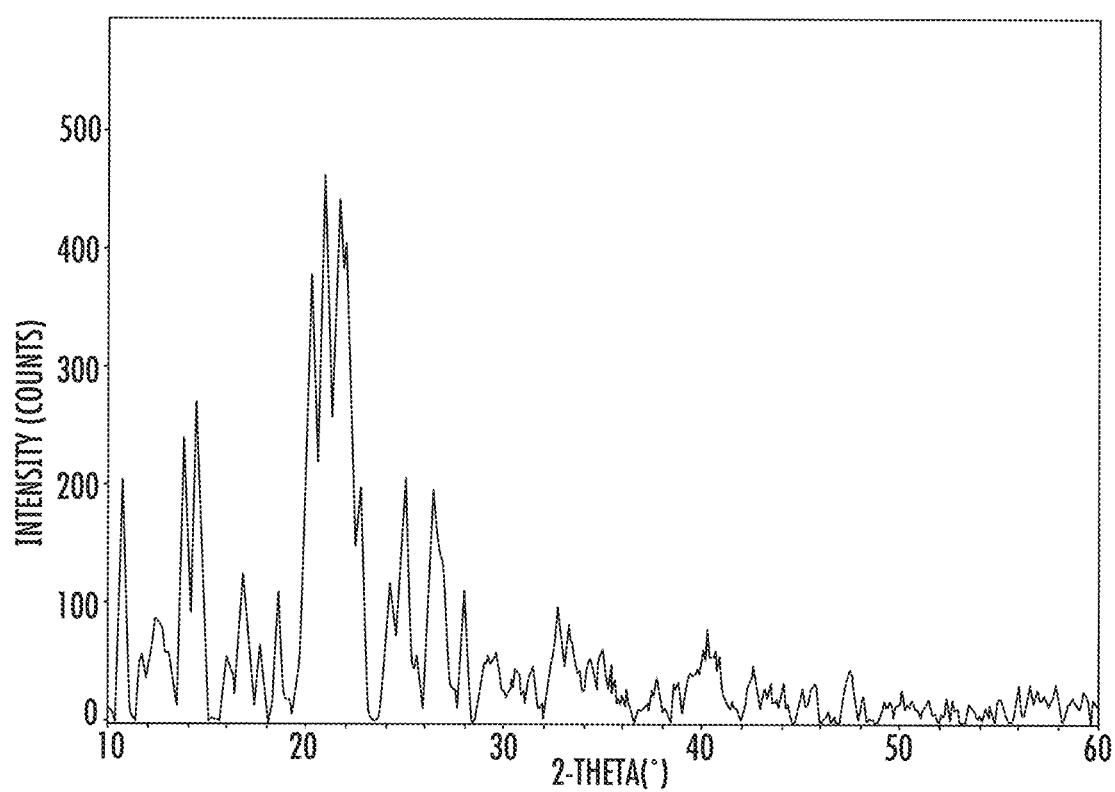

FIG. 5 illustrates the DSC thermogram for the Cepharanthine 2HCl salt. As can be seen, it identifies at least two peaks in the melting endotherms at temperatures in the range of 85° C. to 95° C. (90.44° C. peak identified) and in the range of 255° C. to 265° C. (259.41° C. peak identified). A relatively small endotherm peak is also observed in the range of 175° C. to 185° C. (180.81° C. peak identified). FIG. 6 illustrates the Powder X-Ray Diffraction (PXRD) data for Cepharanthine 2HCl salt recovered from ethyl acetate. As can be seen, the PXRD indicates that a plurality of distinguishing x-ray diffraction peaks at 2 Theta angles of 10-30 degrees as compared to non-distinguishing x-ray diffraction peaks at 2 Theta angles of greater than 30 degrees, wherein said distinguishing x-ray diffraction peaks have relative intensity counts between 150-500 at 2 Theta angles of 10-30 degrees and non-distinguishing x-ray diffraction peaks have relative intensity counts of less than 150 at 2 Theta angles of greater than 30 degrees.

Figure 7:
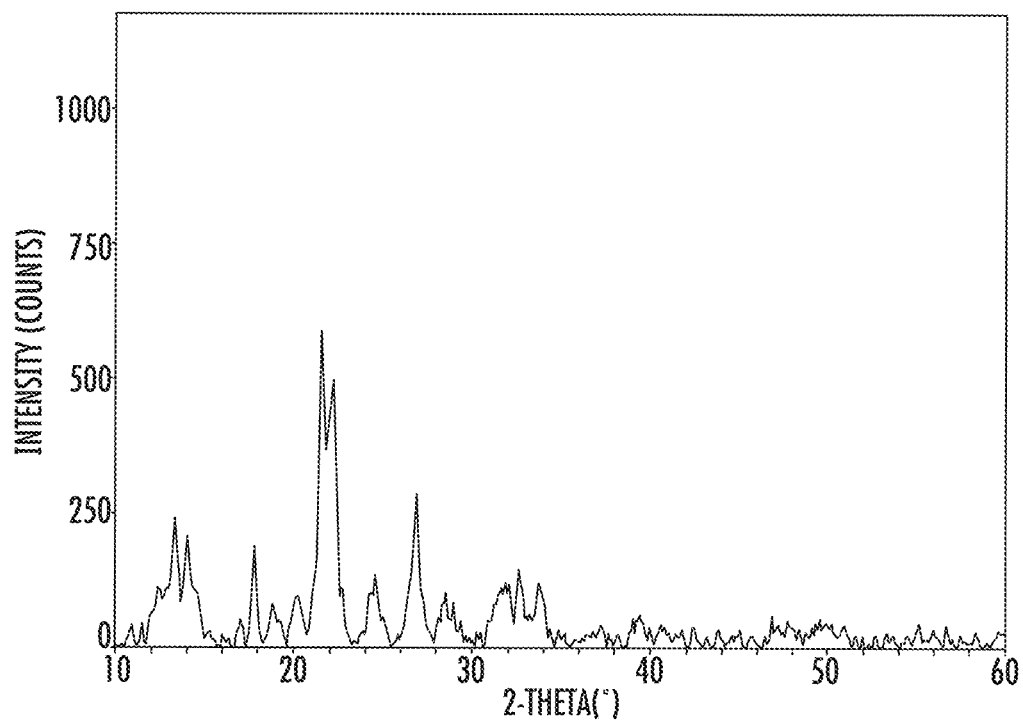
Figure 8:
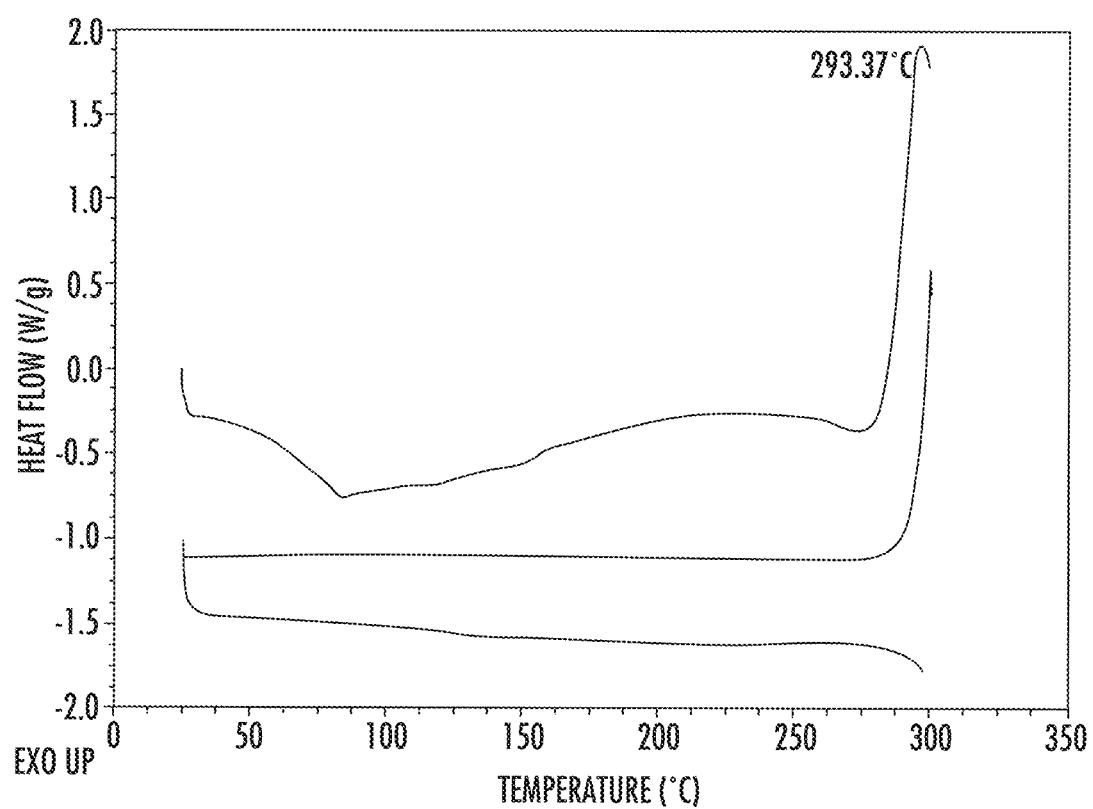

FIG. 7 illustrates the Powder X-Ray Diffraction (PXRD) data for the Cepharanthine 2HBr salt recovered from ethanol-water. As can be seen, the PXRD indicates that a plurality of distinguishing x-ray diffraction peaks at 2 Theta angles of 10-30 degrees as compared to non-distinguishing x-ray diffraction peaks at 2 Theta angles of greater than 30 degrees, wherein said distinguishing x-ray diffraction peaks have relative intensity counts between 200-550 at 2 Theta angles of 10-30 degrees and non-distinguishing x-ray diffraction peaks have relative intensity counts of less than 200 at 2 Theta angles of greater than 30 degrees. FIG. 8 illustrates the DSC thermograph for Cepharanthine 2HBr.

Figure 9:
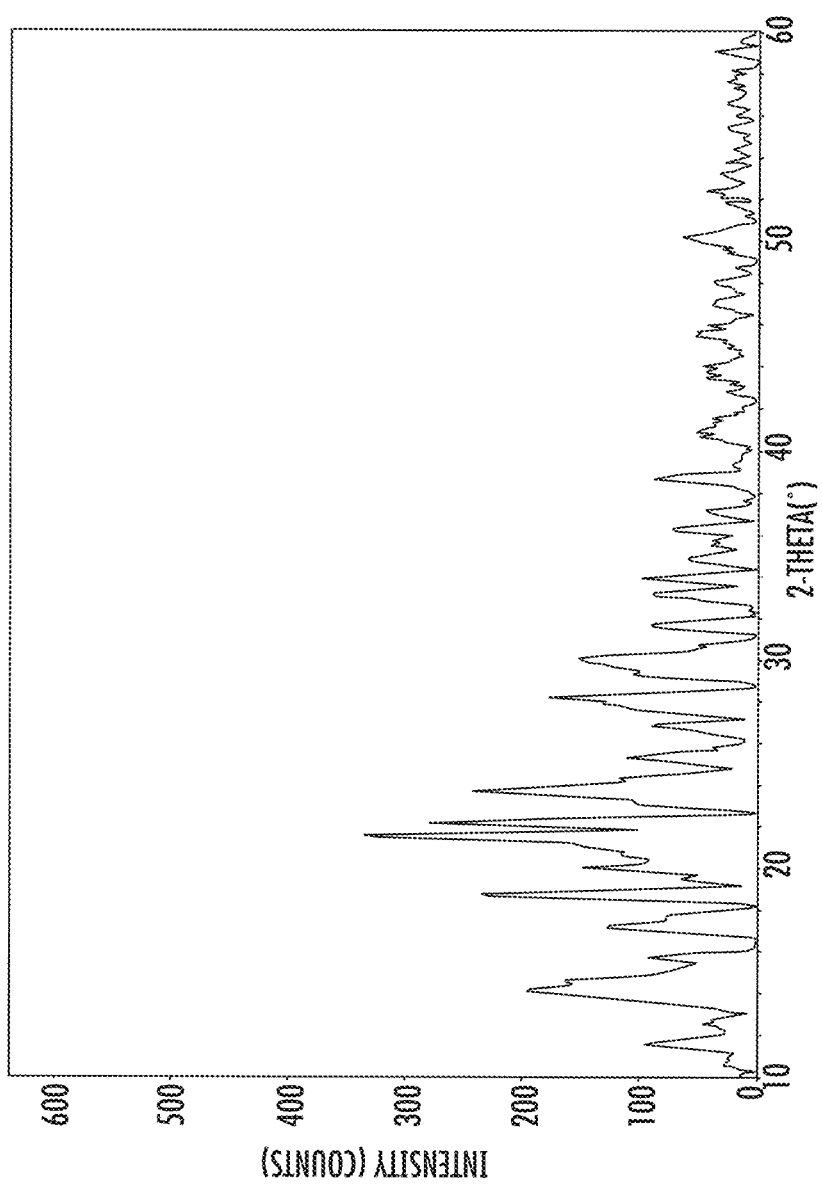

FIG. 9 illustrates the Powder X-Ray Diffraction (PXRD) data for Cepharanthine 2HBr recovered from ethyl acetate. As can be seen, the PXRD indicates that a plurality of distinguishing x-ray diffraction peaks at 2 Theta angles of 10-35 degrees as compared to non-distinguishing x-ray diffraction peaks at 2 Theta angles of greater than 35 degrees, wherein said distinguishing x-ray diffraction peaks have relative intensity counts between 150-400 at 2 Theta angles of 10-35 degrees and non-distinguishing x-ray diffraction peaks have relative intensity counts of less than 150 at 2 Theta angles of greater than 35 degrees.

Figure 10:
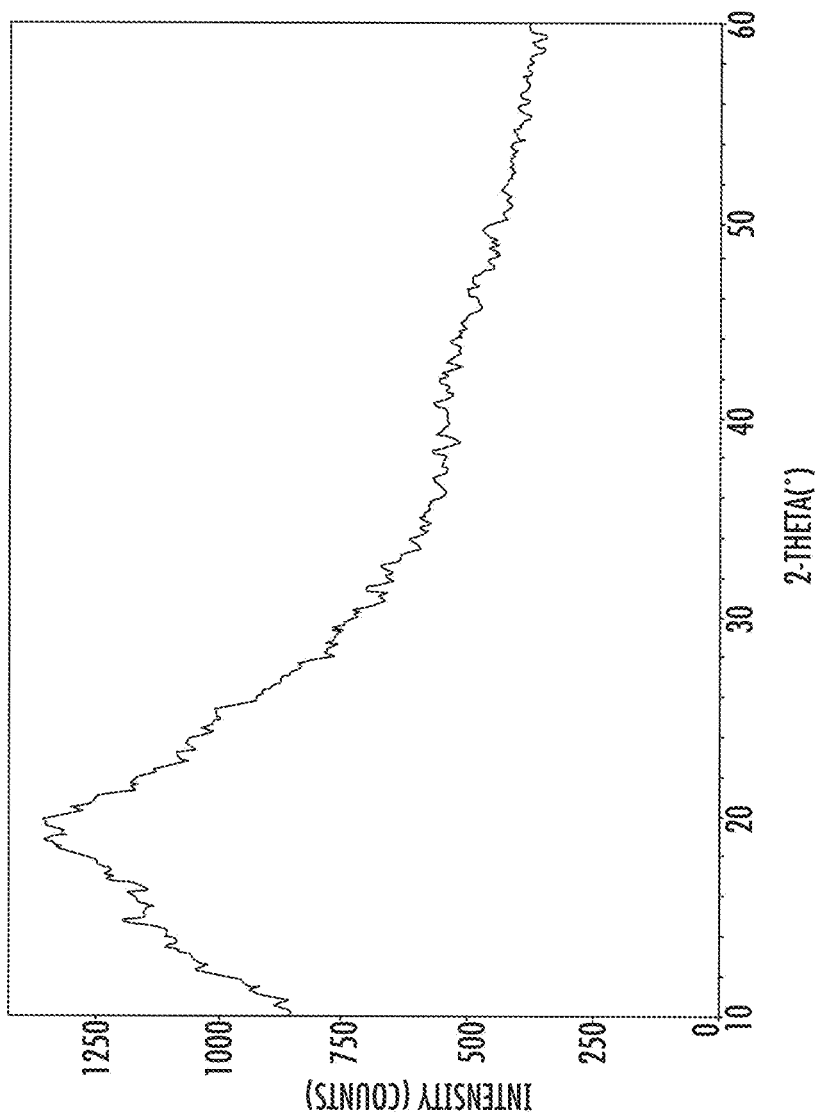
Figure 11:
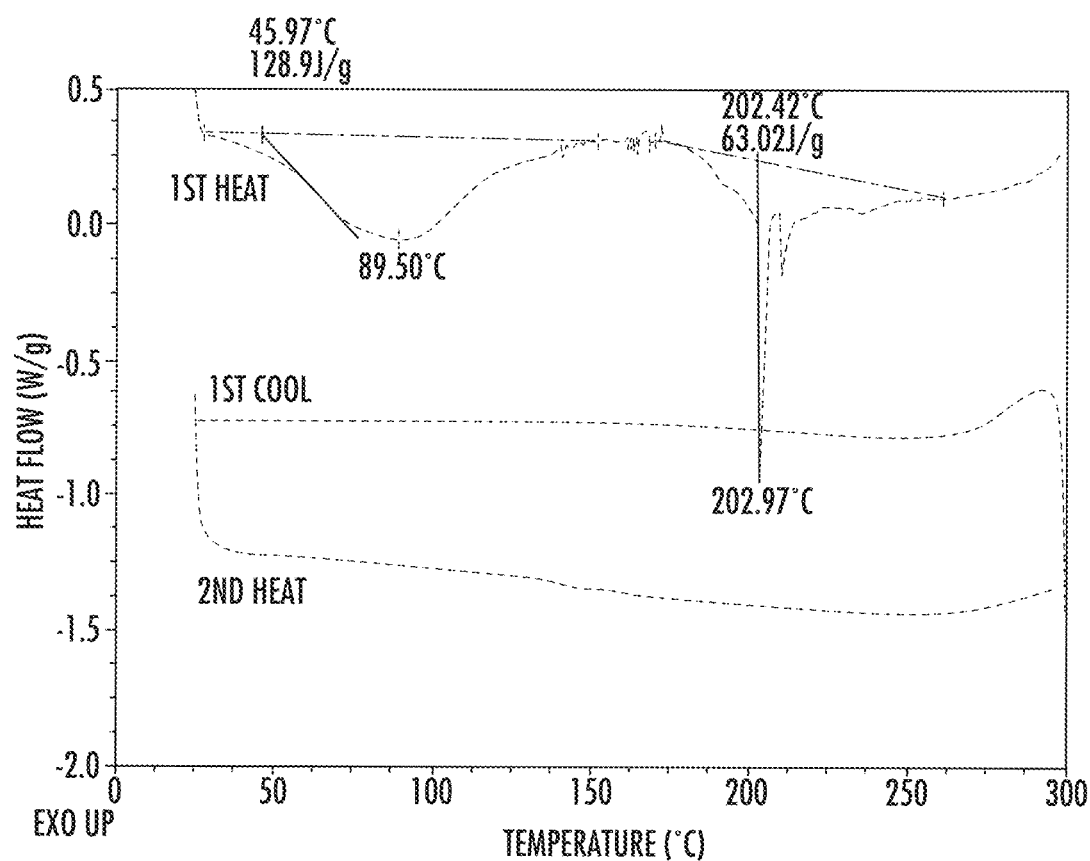

FIG. 10 illustrates the Powder X-Ray Diffraction (PXRD) data for Cepharanthine 2Pyruvic acid. FIG. 11 illustrates the DSC thermograph for Cepharanthine 2Pyruvic acid.

Table 3 below provides the data of three additional samples of Cepharanthine 2HCl recrystallized from ethanol-water.

TABLE 3

Data for CEPN•2HCl Salts Recrystallized from EtOH—$H_2O$

| Sample ID | CEPH•2HCl (g) | Recovery (g) | Recovery (%) |
| --- | --- | --- | --- |
| 1 | 1.0074 | 0.1739 | 17.2 |
| 2 | 1.0077 | 0.4367 | 43.3 |
| 3 | 1.0065 | 0.3651 | 36.3 |

Figure 12:
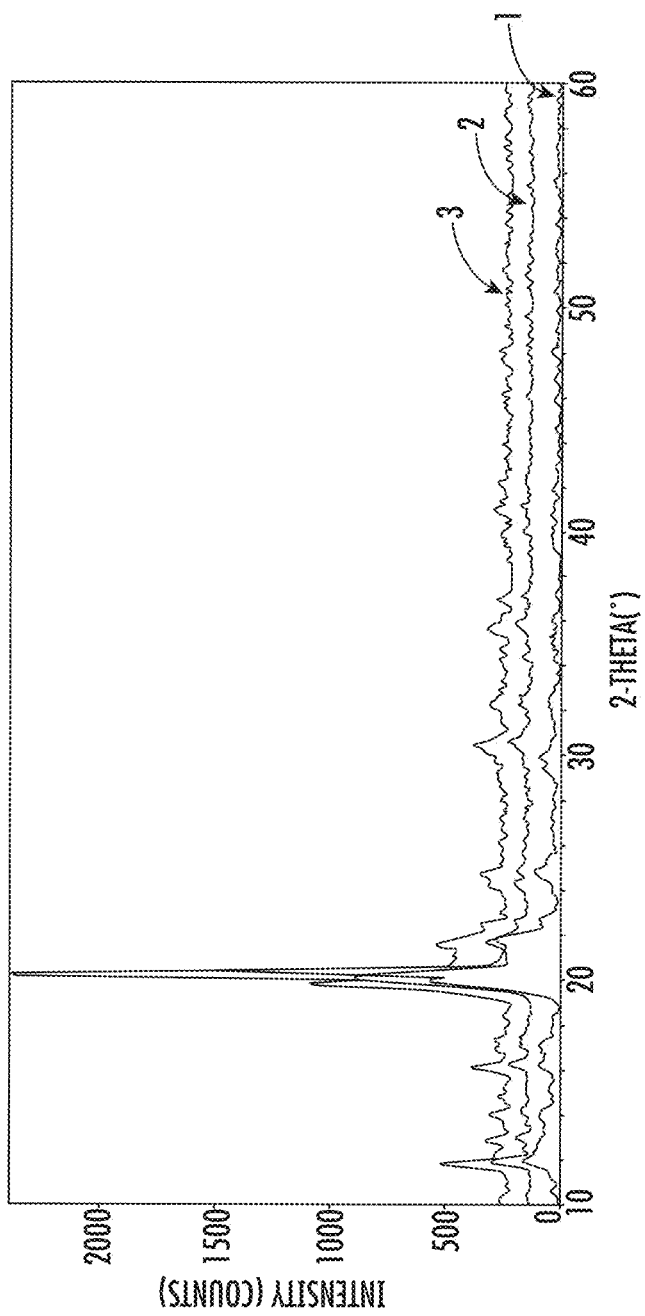

FIG. 12 provides the Powder X-Ray Diffraction (PXRD) data for the three (3) Cepharanthine 2HCl samples noted above in Table 3. As can be seen, the PXRD indicates that a plurality of distinguishing x-ray diffraction peaks at 2 Theta angles of 10-25 degrees as compared to non-distinguishing x-ray diffraction peaks at 2 Theta angles of greater than 25 degrees, wherein said distinguishing x-ray diffraction peaks have relative intensity counts between 500-2500 at 2 Theta angles of 10-25 degrees and non-distinguishing x-ray diffraction peaks have relative intensity counts of less than 500 at 2 Theta angles of greater than 25 degrees.

Figure 13:
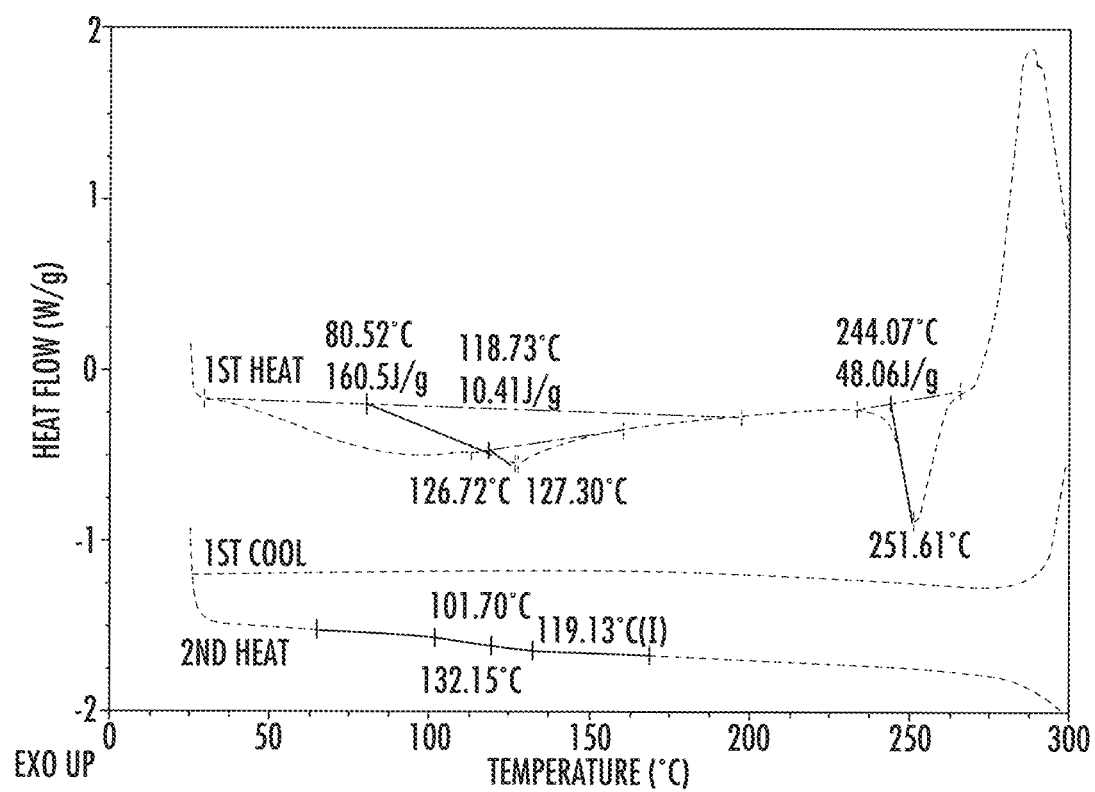
Figure 14:
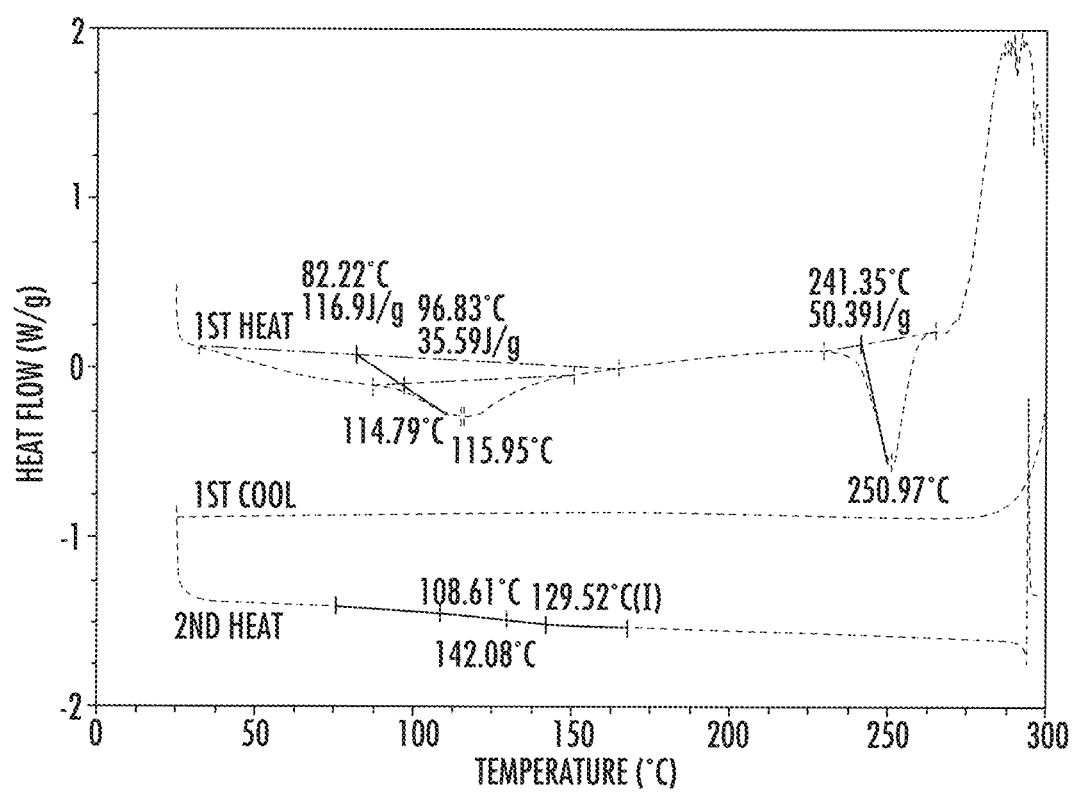
Figure 15:
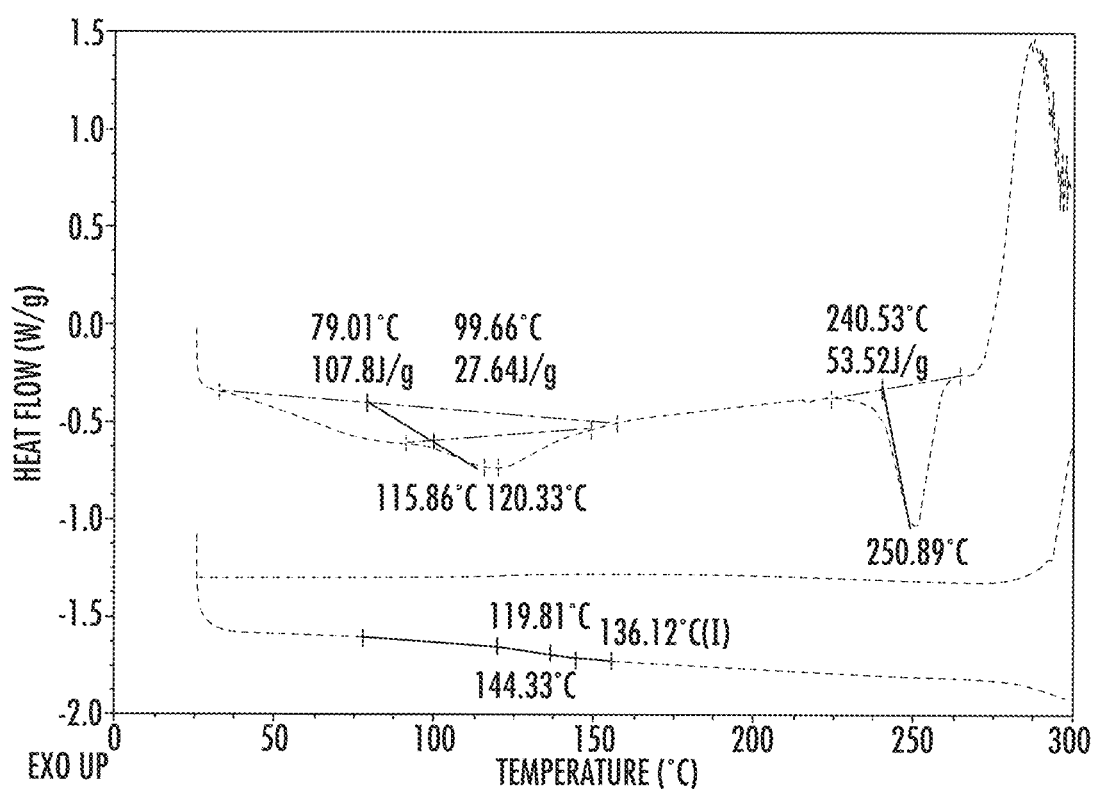
Figure 16A:
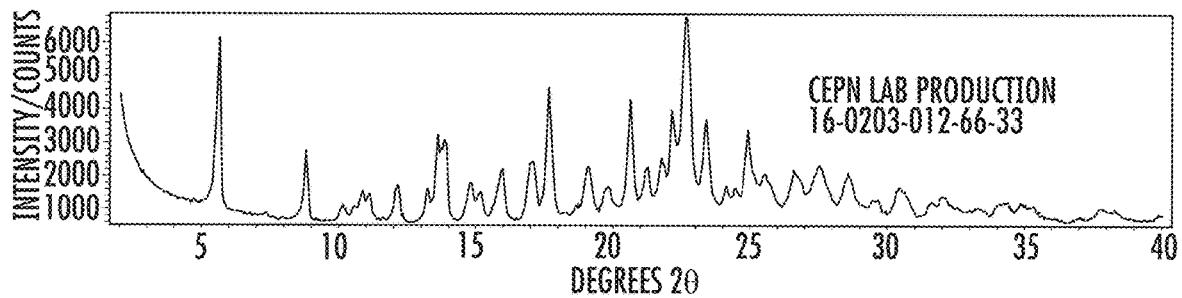
Figure 16B:
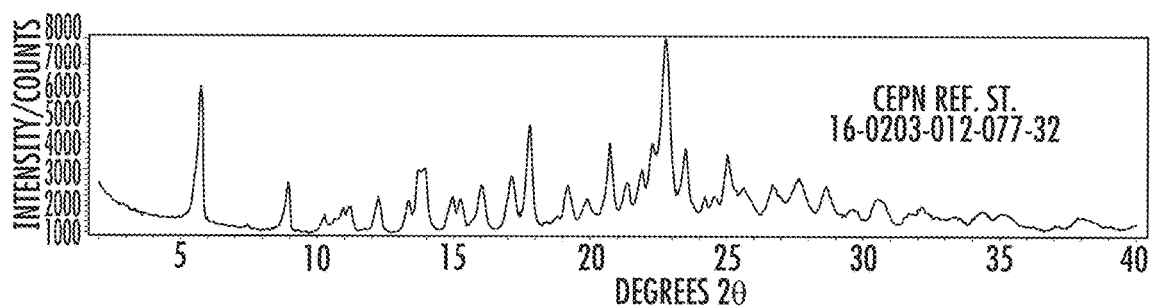
Figure 16C:
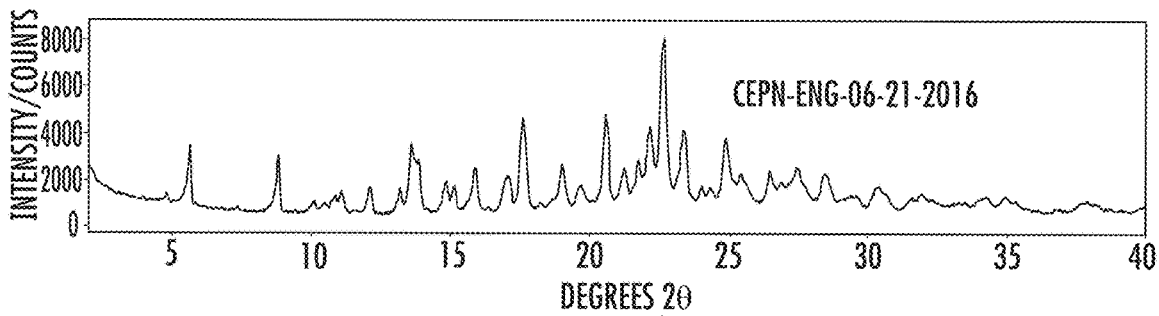
Figure 16D:
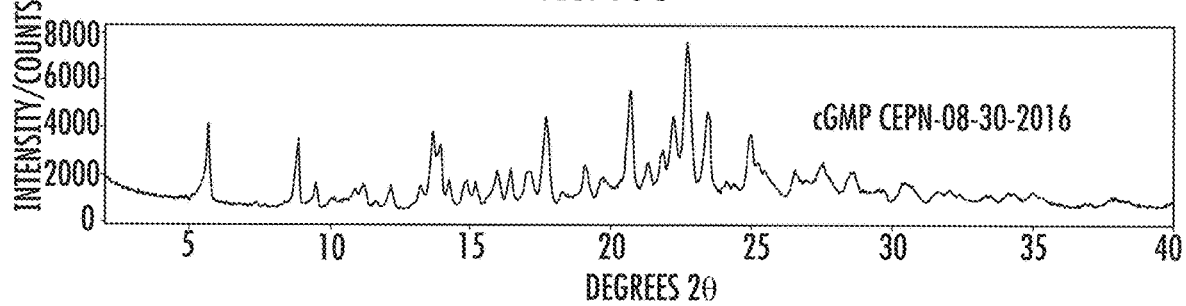

FIG. 13 provides the DSC thermograph of sample 1 from Table 3. FIG. 14 provides the DSC thermograph of sample 2 from Table 3. FIG. 15 provides the DSC thermograph of sample 3 from Table 3.

In one example, Cepharanthine bis-hydrobromide was obtained through the following preferred procedure. To a stirred solution of Cepharanthine (2.2 g, 3.626 mmol) in EtOH (40 mL) was added 2N hydrobromic acid (3.63 mL, 7.252 mmol). The mixture was stirred for 30 minutes. Diethyl-ether was added and the resulting slurry was filtered. The solid was recrystallized from 2-propanol and hexanes to obtain crystalline Cepharanthine bis-hydrobromide (2.27 g, 82%).

In the case of organic acid salts, briefly, the process for the preparation of pyruvic acid salt was accomplished as follows: pure Cepharanthine (1.82 g, 3.0 mmol) was completely dissolved in ethanol (25 mL) and 2 equivalents of pyruvic acid (0.53 g, 6 mmol) in ethanol was added slowly while stirring. Additional ethanol was used to complete the pyruvic acid transfer. The mixture was stirred further 30 min before ethanol was evaporated in reduced pressure. The gummy residue was dissolved again in DCM and evaporated to obtain a foamy solid. The solid was suspended in methyl tert-butyl ether (MTB), MTB supernatant was decanted off to remove excess pyruvic acid if present and remaining solvent was removed with vacuum. Attempts to crystallize the salt using 2-propanol, ethanol, and DCM were unsuccessful. Thus, the purification was completed by precipitation using a DCM/heptane solvent system followed by filtration of the solid, washing the solid with a mixture of solvent systems containing 2-propanol, DCM, and heptanes, and drying the solid under high-vacuum to obtain partially shiny solid (2.14 g, 91% yield). Comparison of $H^1$ NMR spectra of both salt and Cepharanthine (solvent: $CDCl_3$) confirmed the formation of the pyruvic acid salt.

In yet another preferred procedure, Cepharanthine bis-pyruvate was formulated by adding a solution of pyruvic acid (0.528 g, 6.00 mmol) in EtOH (10 ml) to a stirred solution of Cepharanthine (1.82 g, 3.000 mmol) in EtOH (25 mL). The residual pyruvic acid was rinsed with EtOH (5 mL) and added to the Cepharanthine solution. The mixture was stirred for 1 hour and evaporated. The gummy solid was dissolved in dichloromethane and concentrated to afford a solid foam of Cepharanthine bis-pyruvate salt (2.20 g).

Cepharanthine bis-pyruvate was also preferably formulated by slow adding a solution pyruvic acid (27.6 g, 313.200 mmol) in dichloromethane (DCM) (40 mL) to a stirred solution of Cepharanthine (95.0 g, 156.60 mmol) in dichloromethane (DCM) (400 mL). The residual pyruvic acid was rinsed with DCM (50 mL) and added to the Cepharanthine solution. The mixture was stirred for 1 hour and concentrated to afford a light pink solid of Cepharanthine bis-pyruvate salt (122.1 g).

The process for the preparation of salt derivatives of Tetrandrine using various organic and inorganic acids can preferably proceed as follows: the process comprises contacting both tertiary amine groups in the alkaloid Tetrandrine with the selected acid in an appropriate solvent system. All reactions were preferably carried out in ambient temperature and pressure unless noted otherwise. The preferred inorganic acids selected for the final salt formulations were HCl and HBr, which were obtained in either case as 2M solutions. The organic acids selected were preferably methanesulfonic acid (MSA) and pyruvic acid, both of which were liquids. Ethanol was preferred as the common solvent in all preparations, except for that of MSA salt to avoid the known neurotoxic ester formation of MSA with alcohols.

A representative procedure with respect to inorganic acids follows with regard to Tetrandrine bis-hydrobromide (TETN.2HBr). Hydrobromic acid in 48% aq (1.10 ml, 9.67 mmol) is added to a stirred solution of TETN (3.01 g, 4.83 mmol) in DCM 22 (ml) and EtOH (192 ml). The reaction mixture was sealed and stirred at room temperature for 30 minutes and concentrated. The foam was placed on high vacuum overnight to afford yellow solid foam (3.80 g, 100% yield). The solid TETN.2HBr was suspended in and precipitated from various solvents, i.e., isopropyl alcohol (IPA), acrylonitrile (ACN), dichloromethane-methanol (DCM-MeOH), and methanol (MeOH), as set forth in Table 4, below. The crystallization products are also discussed in Table 4 below.

TABLE 4

TETN-2HBr Crystallization Conditions and Data

| Crystallization Solvent | Crystallization Conditions (mg of TETN•2HBr in ml solvent) | Material after Crystallization | Micrographs |
|---|---|---|---|
| Isopropyl Alcohol | 142 mg in 13 ml | Yellow Needles | Crystalline |
| Acrylonitrile | 20 mg in 5 ml heated | Light Yellow Solid | Glass |
| Dichloromethane-Methanol | 270 mg in (3 ml:1 ml) DCM:MeOH, respectively | | Glass/Crystalline |
| Methanol | 28.2 mg in 0.5 ml, heated to dissolve and slow evaporation | White Solid | NA |

A representative process for the preparation of Tetrandrine bis-phosphate (TETN.2H$_2$PO$_4$) is discussed further herein. Phosphoric acid in 85% aq. (0.53 ml, 7.83 mmol) was added to a stirred solution of Tetrandrine (2.44 g, 3.92 mmol) in dichloromethane (DCM) (40 ml) and ethyl alcohol (EtOH) (150 ml). White precipitate immediately formed. The reaction mixture was sealed and stirred at room temperature for 40 minutes and concentrated. The solid was placed on high vacuum overnight to afford white powder solid (3.22 g, 100% yield). The process was repeated for other solvents, i.e., isopropyl alcohol (IPA), dichloromethane-methanol (DCM-MeOH), methanol (MeOH), ethanol-methanol (EtOH-MeOH) solvent systems, as outlined in Table 5 below.

TABLE 5

TETN•2H$_2$PO$_4$ Crystallization Conditions and Data

| Crystallization Solvent | Crystallization Conditions (mg TETN•2H$_2$PO$_4$ in ml solvent) | Material After Crystallization | Micrographs |
|---|---|---|---|
| IPA | 100 mg in 20 ml, heated (1.5 week slow evaporation) | White Solid | Crystalline |

TABLE 5-continued

TETN•2H$_2$PO$_4$ Crystallization Conditions and Data

| Crystallization Solvent | Crystallization Conditions (mg TETN•2H$_2$PO$_4$ in ml solvent) | Material After Crystallization | Micrographs |
|---|---|---|---|
| DCM-MeOH | 400 mg in 50 ml (25 ml:25 ml) DCM:MeOH, respectively, heated (slow evaporation) | Light Pink Solid | Crystalline + Glass |
| MeOH | 125 mg in 10 ml MeOH, heated (slow evaporation) | Light Pink Solid | Crystalline + Glass |
| EtOH—MeOH | 26 mg in 7 ml (5 ml:2 ml) EtOH:MeOH, respectively, (slow evaporation) | White Solid | Glass |

Tetrandrine bis-hydrochloride was prepared according to the following representative procedure. To a stirred solution of Tetrandrine (2.49 g, 4.000 mmol) in ethanol (EtOH) (25 mL) was added 2N hydrochloric acid in diethyl ether (4.40 mL, 8.800 mmol) slowly resulting in a light brown precipitate. The precipitation was completed by adding methyl tert-butyl ether (MTB). The slurry was filtered and washed with 2 times with MTB. The solid was allowed to air dry to afford Tetrandrine bis-hydrochloride salt (3.30 g, 119%).

A further representative process to provide Tetrandrine bis-sulfate was prepared as follows. To a stirred solution of Tetrandrine (3.0 g, 4.817 mmol) in ethanol-dichloromethane (EtOH-DCM) (100 mL/20 mL) was added dropwise 18M sulfuric acid (0.535 mL, 9.634 mmol). The mixture was stirred overnight. The resulting white slurry was filtered to afford Tetrandrine bis-sulfate (3.28 g). Next, 640 mg of the solid was slurried with DCM (4 mL) and dissolved by adding MeOH (0.4 mL). The solution was slowly stirred and allowed to evaporate overnight resulting in white solid. A micrograph was obtained of the solid.

In the case of organic acids, a representative process for the preparation of Tetrandrine bis-methanesulfonate (TETN.2MSA) is discussed further herein. To a stirred solution of Tetrandrine (2.50 g, 4.01 mmol) in dichloromethane (DCM) (40 ml) was added methane sulfonic acid (MSA) (0.52 ml, 8.03 mmol). The reaction mixture was sealed and stirred at room temperature for 60 minutes and concentrated. The solid foam was placed on high vacuum overnight to afford yellow solid foam (3.20 g, 100% yield). The TETN.2MSA was crystallized by adding 1:1 ethanol (EtOH) and acetone (3 ml each) to a 40 ml vial of TETN.2MSA, which was then heated until the TETN.2MSA dissolved. The solution was then allowed to slowly evaporate in a fume hood for better air circulation to obtain white solid powder. Micrograph confirmed this provided a crystalline salt.

In another embodiment, the TETN.2MSA was dissolved in ethanol (EtOH). Hexane was added as an anti-solvent to provide a white precipitate. The mixture was allowed to slowly evaporate while cap off and letting air circulate in a fume hood to obtain a white powder. Micrograph analysis indicated the formation of crystals.

Table 6 outlines conditions for crystallization of the TETN.2MSA using ethanol-acetone, methanol, ethanol-hexane, water and ethanol.

TABLE 6

Crystallization Conditions and Data

| Crystallization solvent | Crystallization Conditions (mg of TETN•2MSA in ml of solvent) | Material after Crystallization | Micrographs |
|---|---|---|---|
| EtOH-Acetone | 310 mg in 6 ml EtOH:acetone (3 mL:3 mL), dissolved with heat and slow evaporation | White solid powder | Crystalline |
| MeOH | Heated to dissolve then slow evaporation | Clear oil | NA |
| EtOH-Hexane | Dissolved in EtOH and added hexane as a antisolvent to get ppt, slow evaporation | White solid powder | Crystalline |
| H$_2$O | 84 mg dissolved in 0.5 mL H$_2$O with slow evaporation | Oil/gummy | NA |
| EtOH | Dissolved in EtOH heated to dissolve, slow evaporation | White solid powder | NA |

Powder X-ray Diffraction (PXRD) analysis indicates that triclinic crystals were obtained for the ethanol-acetone process conditions of Table 6 above.

A representative process for the preparation of Tetrandrine bis-lactic acid (TETN-2LA) is discussed further herein. Lactic acid (0.65 ml, 8.70 mmol) was added to a stirred solution of Tetrandrine (2.70 g, 4.35 mmol) in dichloromethane (40 ml). The reaction mixture was sealed and stirred at room temperature for 60 minutes and concentrated. The solid foam was placed on high vacuum overnight to afford white solid foam (3.50 g, 100% yield).

Table 7, below, provides crystallization conditions and observations using water, acetone-hexane, methanol (MeOH), isopropyl alcohol (IPA), ethanol-hexane (EtOH-hexane) and ethanol (EtOH) solvent systems.

TABLE 7

Crystallization Conditions and Data

| Crystallization Solvent | Crystallization Conditions (mg of TETN•2LA in mg solvent) | Material after Crystallization | Micrographs |
|---|---|---|---|
| H₂O | 73 mg in 0.5 mL H₂O (1.5 weeks slow evaporation) | Light peach glass solid | Crystals within glass |
| H₂O | 382 mg in 1.0 mL H₂O (slow evaporation) | Light peach glass solid | Crystalline |
| Acetone-Hexane | 50 mg in 3 ml acetone:hexane (1 ml:2 ml), respectively | Light peach glass solid | Crystalline + Glass |
| MeOH | Slow evaporation | Oil | NA |
| IPA | Slow evaporation | Oil | NA |
| EtOH-Hexane | 78 mg in 3 ml EtOH:Hexane (1 ml:2 ml), respectively | Gummy-oil | NA |
| EtOH | 20 mg in 0.5 mL heated to dissolve and slow evaporation | Oil | NA |

Tetrandrine bis-pyruvate was formed by slowly adding a solution of pyruvic acid (14.118 g, 160.328 mmol) to a stirred solution of Tetrandrine (49.922 g, 80.164 mmol) in dichloromethane (DCM) (200 mL). The residual pyruvic acid was rinsed with dichloromethane (DCM) (25 mL) and added to the Tetrandrine solution. The mixture was stirred for 1 h and then concentrated to afford a solid foam. The foam was placed on the high vacuum overnight. The solid was then slurried with diethyl ether (200 mL) at room temperature for 20 minutes and filtered. The solid was placed onto the high vacuum over the weekend. The solid was then dissolved in ethanol (EtOH) (200 mL) and concentrated. The semi-solid foam was triturated with diethyl ether (100 mL) and concentrated. The solid was then placed onto high vacuum overnight to afford Tetrandrine bis-pyruvate (TETN bis-pyruvate) (60.15 g, 94%).

Tetrandrine bis-citrate was formed in an exemplary method as follows. To a stirred solution of Tetrandrine (3.0 g, 4.817 mmol) in ethanol-dichloromethane (EtOH-DCM) (100 mL/20 mL, respectively) was added solid citric acid (1.851 g, 9.634 mmol). The slurry was stirred at room temperature for 5 minutes and then water (10 mL) was added. The homogenous solution was stirred for 1 hour and was then concentrated to give a viscous oil. The oil was triturated with methyl tert butyl ether (1000 mL) resulting in a solid. Next, 180 mg of the solid was dissolved in hot 1:1 EtOH:Acetone (4 mL:4 mL, respectively) and allowed to cool with stirring. The resulting precipitate was centrifuged and the solvent decanted. A micrograph was obtained of the solid. Powder X-ray diffraction (PXRD) indicated amorphous material.

As can be appreciated from the above, another preferred process to make a reference standard CEPN.2HCl polymorph composition is now shown in Scheme 1. In the first step, cepharanthine (CEPN) (1) is preferably dissolved in ethyl acetate and two equivalents of concentrated HCl are added dropwise. The solution is allowed to stir over night at room temperature. After removal of solvent the yield of CEPN.2HCl 2) is 89.0%. In step two, 2 is preferably dissolved in ethanol-water, i.e., EtOH:H₂O (93:7) at 70° C. The solution is gradually cooled and at 21° C. crystallization occurs. The recovery of 3 is 69.3%. Accordingly, the recrystallization solution herein for recovery of 3 is preferably an aliphatic alcohol such as ethanol in excess to water, such as 80-99 parts aliphatic alcohol to 1-20 parts water.

A quantity of CEPN.2HCl (4.965 kg, lot CEPN 06212016) was synthesized for use in pre-clinical animal testing. This material was determined to have excellent purity (99.4%) and quality. The material processed well, although more aggressive filtration techniques (centrifugation) is preferably required for good dewatering, and more aggressive drying techniques (cake temperature >60° C.) is preferred to remove residual solvent (ethanol) to less than 2% by weight.

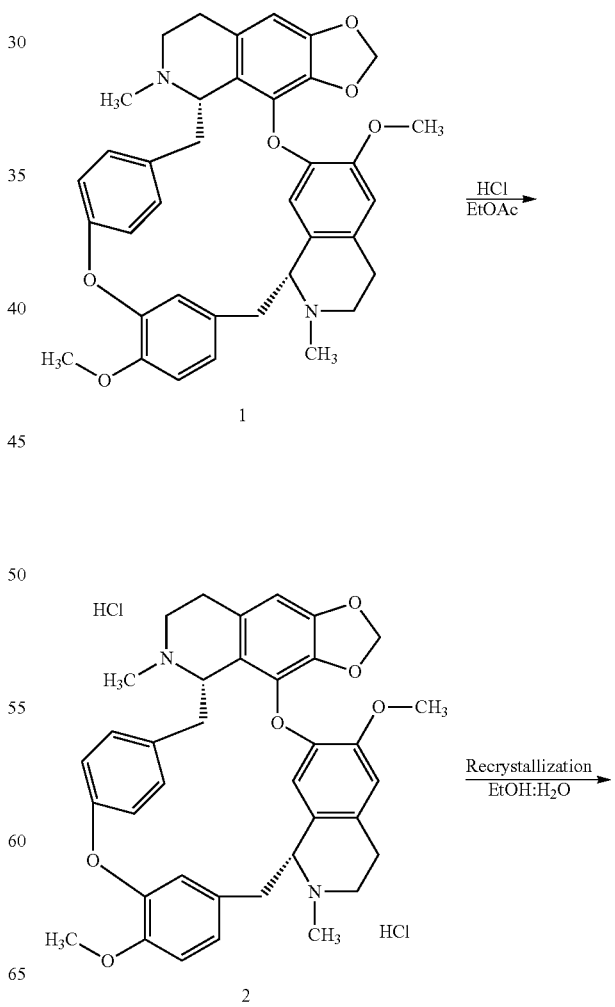

Scheme 1. Preparation of CEPN•2HCl Reference Standard

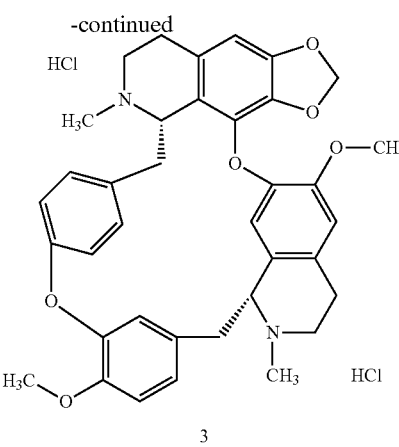

3

Example 1

Preparation of CEPH.2HCl (2) Polymorphs Salt Formation

A 2 L three neck round bottom flask was charged with CEPN (1, 100.82 g, 0.166 mol, LIMS #57476, Aktin Chemicals, Inc.), a mechanical stirrer (60 rpm), $N_2$ inlet and ethyl acetate (1184.2 g, 13.4 mol). Once 1 was dissolved, HCl (28.4 mL, 12.0 M, 2.05 equiv., LIMS #53304, Fisher Certified ACS, plus) was added dropwise via glass pipette over thirty minutes. The salt precipitated out after several minutes during the addition. The slurry was allowed to stir for 16 h. The slurry was filtered using a fritted Buchner funnel. The solid was washed four times with cold (ice bath, 0° C.) ethyl acetate (478.2 g, 368.4 g, 433.8 g and 478.3 g; respectively). The solid was collected in a 1 L round bottom flask and put on the high vacuum line overnight (0.1 Torr, 16 h). After removal of solvent, a white solid (2, 102.2 g, SwRI Lot #16-0203-012-037-10, 89.0%) was collected.

Recrystallization of CEPN.2HCl (3) Reference Standard

A 2 L jacketed reactor with a five port lid was charged with CEPN.2HCl (2, 60.0 g, 0.0883 mol, SwRI lot #16-0203-012-037-10), a mechanical stirrer (60 rpm), $N_2$ inlet and a thermocouple. A 540 mL solution of EtOH/DI $H_2O$ with a 93:7 ratio was prepared by mixing 38 mL of DI water to 502 mL EtOH (200 proof, LIMS #69292, Pharmco-AAPER). The jacketed flask was connected to a recirculating chiller and heated to 70° C. for 0.5 h. The solution was gradually cooled (3 h) and crystallization occurred at 21.0° C. The slurry was transferred to a 600 mL glass funnel with a glass frit. The flask was washed with 150 mL of cold (ice bath, 0° C.) 200 proof EtOH. The solid was added to a 1 L round bottom flask and placed on the high vacuum line overnight (0.1 Torr, 16 h). The solid was transferred to a plastic container and the larger chunks were broken up with a mortar. The solid was transferred back to a flask and placed under a high vacuum line for further drying (24 h). After drying to completeness (no further weight change), a white solid (3, 41.6 g, 0.0612 mol, SwRI Lot #16-0203-012-077-32, 69.3% recovery) was collected.

Example 2

Scaled 5 kg CEPN.2HCl Engineering Run (ENG)

CEPN.2HCl is can also be produced at the 5 kg scale (and by current good manufacturing practice [cGMP] at the 10 kg scale) by addition of HCl (aq) to the free base CEPN in EtOAc (designated Step 1, Scheme 1). The resulting solids are dried and then purified by recrystallization in absolute ethanol/water. The chemistry is detailed in Table 4 below. Table 5 identifies the preferred source of raw materials.

TABLE 4

| | amt (gm) | purity (%) | FW (gm/mol) | density (gm/cm³) | mol | molar equiv | volume (mL) | Block Flow |
|---|---|---|---|---|---|---|---|---|
| material | | | | | | | | |
| Cepharanthine (CEPN) | 7346 | 98% | 606.71 | | 11.87 | L.R. | | Dissolve CEPN in EtOAc in reactor |
| ethyl acetate | 58667 | 100% | 88.11 | 0.902 | 665.84 | 56.11 | 65041 | Slowly add the HCL to the reactor and allow to stir overnight |
| hydrochloric acid, 37% | 2444 | 37% | 36.46 | 1.200 | 24.81 | 2.09 | 2037 | Filter by cetrifugation |
| ethyl acetate | 20449 | 100% | 88.11 | 0.902 | 232.09 | 19.56 | 22671 | Slurry solids in EtOAc to wash, then filter again, collect and dry solids to constant weight |
| Step 2 Recrystallization | | | | | | | | |
| CEPN 2 HCL | 8088 | 100% | 681.64 | | 11.87 | L.R. | | Add CEPN HCL crude to water and EtOAc, then heat to 70° C. to dissolve and perform hot filtration |

TABLE 4-continued

| | amt (gm) | purity (%) | FW (gm/mol) | density (gm/cm$^3$) | mol | molar equiv | volume (mL) | Block Flow |
|---|---|---|---|---|---|---|---|---|
| 93:7 EtOH/Water Soln. | | | | | | | | Cool to <30° C. ON to crystallize |
| ethanol 200 proof | 53528 | 100% | 46.07 | 0.791 | 1161.88 | 97292 | 67671 | Filter solids by centrifucation, then slurry to wash in COLD EtOH and filter again |
| water | 5123 | 100% | 18.00 | 1.00 | 284.59 | 23.98 | 5123 | |
| ethanol 200 proof | 15994 | 100% | 46.07 | 0.791 | 347.18 | 29.26 | 20221 | Dry solids ON at >60° C. cake temperature with nitrogen purge, then sieve through 20 mesh to break up clumps and dry for an additiona 2-3 days (EtOH <3%) |
| product | | | | | | | | |
| CEPN 2HCL | 4966 | 100% | 681.64 | 0.872 | 7.286 | 61.4% | | |

TABLE 5

CEPN Raw Materials

| Material | CAS | Supplier | Grade | Lot |
|---|---|---|---|---|
| Cepharanthine | 481-49-2 | Aktin Chemicals | 98% | CE-160328 |
| Ethanol (200 proof) | 64-17-5 | Pharmco-Aaper | ACS/USP | K16D15234 |
| Water (WFI) | 7732-18-5 | Corning | WFI | 22415007 |
| Hydrochloric acid | 7647-01-0 | Fisher Scientific | Cert. ACS | 157205 |
| Ethyl Acetate | 141-78-6 | Pharmco-Aaper | Reagent ACS | C15I21008 |

CEPN.2HCl Crude Product Synthesis

CEPN (7.355 kg, 11.88 mol, L.R.) was added to Ethyl Acetate (58.6 kg) and stirred in a 200 L cylindrical reactor. 37% aqueous HCl (2.510 kg, 25.49 mol, and 2.15 eq.) was then added slowly over 70 min with a 6.4° C. temperature rise. The mixture was stirred overnight, and then filtered in portions by centrifugation. The dewatered material was then slurried in Ethyl Acetate (20.55 kg) and re-centrifuged. The dewatered solids were then collected in a 50 L Nutsche filter for drying. The jacket was controlled at approximately 50° C., and a vacuum of 27 in HG was applied with a nitrogen purge flow of about 15 LPM for an approximate 5 day period. The solids were then sampled then double bagged and placed inside a 5 gal bucket with desiccant pouches.

A total of 8.045 kg of crude CEPN.2HCl (theoretical 8.265 kg, yield of 97.3%) was packaged for further processing. A quantity of the material (218.90 g) was kept for testing and retain.

CEPN.2HCl Recrystallization of Crude CEPN

Crude CEPN.2HCl (8.040 kg, 11.80 mol, L.R.) was added to Absolute Ethanol (53.0 kg) and WFI (5.14 kg) and stirred in a 200 L cylindrical reactor. The mixture was heated to 70.1° C. over 1.5 h to full dissolution. The mixture was then filtered hot, and stirred overnight. The mixture formed a slurry containing white solids by the next morning (crystallized at 21.9° C.). Filtration was done first in a Nutsche filter to remove the mother liquor.

The dewatered solid material was then slurried in ethanol (14.10 kg) and centrifuged. The solids were then collected in a 50 L Nutsche filter for drying. The jacket was controlled at approximately 50° C., and a vacuum of 27 in Hg was applied with a nitrogen purge flow of about 15 LPM (liters/min) for an approximate 6 day period. The solids were then sampled then double bagged and placed inside a 5 gal bucket with desiccant pouches.

A total of 5.337 kg of purified CEPN.2HCl (theoretical 8.155 kg, yield of 65.7%) was packaged. A quantity of the material (18 g) was kept for testing and retain. Subsequent testing showed that ethanol was still present in ~10% by weight. A subsequent evaporative re-processing was done at higher temperature to reduce this amount.

The material (5.310 kg) was put though a #20 mesh sieve to declump and then back into a 50 L Nutsche filter for additional processing. The filter was equipped with internal temperature monitoring to determine the cake temperature at the middle and near the wall. Initially the jacket temperature was set to 80° C. (cake temperature of 52-55° C.). The following day the jacket temperature was increased to 100° C. resulting in a cake temperature of about 65-72° C. This temperature was maintained for 2 additional days with a minimal flow of nitrogen (<5 LPM) at a vacuum level of about 27 in Hg before the heating was halted.

Example 3. Polymorphic Structure of CEPN.2HCl

A well characterized, non-GMP 5 kg batch of CEPN.2HCl for pre-clinical studies and a 10 kg cGMP batch were produced. This effort initially involved (1) HCl precipitation of CEPN.2HCl from ethylacetate solution of CEPN and (2) recrystallization of this precipitate from 90% EtOH/10% water under a variety of conditions and (3) post-equilibration of saturated suspensions of these salts at room temperature and 70° C. to produce a thermodynamically stable polymorph mixture that could be generated on demand in the non-GMP 5 kg and cGMP 10 kg downstream. This aspect is of some importance since, even though CEPN.2HCl is highly soluble in water, potential oral formulations used in the Phase 1 clinical trials could require solid CEPN.2HCl powder formulations in gel caps. Different polymorphic forms of the same compound can have different bioavailability because of different dissolution/recrystallization rates and equilibria. This situation holds even for soluble hydrochloride salts of drugs. In other words, the product generated could consist of a mixture of kinetically preferred and thermodynamically stable crystalline polymorphs in addition to amorphous material. Reference to polymorph is therefore reference to the feature of different crystal forms of the recrystallized CEPN 2HCl recovered herein.

The polymorph distribution (as determined by X-ray diffraction) of the 10 kg cGMP batch (CEPN.08-30-2016), 5 kg engineering batch (CEPN-ENG-06-21-2016, 16-0203-012-119-35) and lab production (16-0203-012-66-33) and "reference standard" (16-0203-012-077-32) were all relatively similar. Both the lab production and reference standard were ethanol recrystallized from the 100 g CEPN.2HCl batch 16-0203-012-037-10, which had been crystallized from ethylacetate. Taking into account only the most relevant six 2Θ values below (Table 6) the following polymorph distribution (A, B, C, D, E, F) was determined to be:

TABLE 6

Relative Diffraction Peak Intensity of Polymorphs A-F

|  | F | A | E | C | B | D |
| --- | --- | --- | --- | --- | --- | --- |
| 2Θ | 4.9 | 5.5 | 7.5 | 8.5 | 8.9 | 9.4 |
| cGMP | – | +++ | – | – | ++ | + |
| ENG | + | +++ | – | – | ++ | – |
| Lab Prod | – | +++ | – | – | ++ | – |
| Ref Std | – | +++ | – | – | ++ | – |

In the above, cGMP is reference to Current Good Manufacturing Practice protocols, ENG is reference to Engineering Batch production (Scheme 1, 5 kg batch), Lab Prod. is reference to laboratory production of 50 g-100 g sample and Ref. Std is a repeat synthesis at the Lab Prod. Scale that was retailed for physiochemical analysis. The designation "–" is identification of relative minor presence of the identified peak, and "+" and "++" and "+++" indicate relatively higher diffraction peak intensities.

As can be observed, different polymorphs were assigned to each 2θ since the relative intensities of all these lower angle reflections appeared to be independent of each other across the samples recrystallized. All of the above samples exhibited essentially the same polymorph distribution (A and B) except that the cGMP run showed a small amount of polymorph D while the ENG run showed a relatively small amount of polymorph F. FIGS. 16A, 16B, 16C and 16D illustrate the x-ray powder diffraction patterns of the polymorph distribution for the CEPN lab production, CEPN reference standard, a 5 kg Engineering production and a 10 kg cGMP production, respectively.

Below is a report on samples that were ethanol crystallized from the 150 g CEPN.2HCl batch 16-0203-012-082-10, which had been also crystallized from ethylacetate. 088-16 is the first crop from ethanol and 089-10 is the second ethanol crop (second recrystallization). The second crop contained A, C and D, but had no B and had a sharper diffraction pattern indicating relatively larger size/more defect free crystals. Sere Table 7, the relative intensity designations the same as noted above in Table 6:

TABLE 7

|  | F | A | E | C | B | D |
| --- | --- | --- | --- | --- | --- | --- |
| 2Θ | 4.9 | 5.5 | 7.5 | 8.5 | 8.9 | 9.4 |
| 16-0203-012-088-16 | – | +++ | – | ++ | + | ++ |
| 16-0203-012-089-10 | – | +++ | – | ++ | – | ++ |

Other samples produced under the Scheme I recrystallization protocol herein are listed below in Table 8, where the relative intensity designations are again the same as those identified in Table 6:

TABLE 8

|  | F | A | E | C | B | D |
| --- | --- | --- | --- | --- | --- | --- |
| 2Θ | 4.9 | 5.5 | 7.5 | 8.5 | 8.9 | 9.4 |
| 16-0203-012-106-27 | + | ++ | ++ | ++ | – | ++ |
| 16-0203-012-097-27 | – | ++ | ++ | ++ | – | ++ |
| 16-0203-012-098-10 | – | ++ | ++ | ++ | – | ++ |
| 16-0203-012-098-27 | – | + | ++ | + | + | ++ |
| 16-0203-012-096-22 | – | + | + | – | – | +++ |
| 16-0203-012-104-23 | – | – | + | – | + | +++ |
| 16-0203-012-096-22 | – | + | + | – | – | +++ |
| 16-0203-012-107-19 | – | ++ | – | ++ | – | ++ |
| 16-0203-012-107-28 | + | ++ | + | ++ | – | ++ |
| 16-0203-012-105-23 | – | ++ | + | ++ | – | ++ |

As can be seen from the above, six polymorphs of CEPN.2HCl can be produced, even upon recrystallizing the ethyl acetate crystallized material from ethanol/water. No single polymorphs have been produced with any of the crystallization processes and all samples produced are mixtures. In addition, some broad background scattering in some of the samples indicates that some amorphous species are also present. In order to produce the scaled ENG and cGMP samples it was preferable to control the crystallization/purification processes as outlined above to reproduce the same polymorph distribution independent of scale.

Example 4. Liquid Crystalline Structure of CEPN.2HCl in Water

Oral dosing of concentrated CEPN.2HCl water solutions of the ENG sample resulted in a complicated phase behavior which involved gelation in the stomach of the rat test animals and resultant toxic effects. The phase behavior of CEPN.2HCl was studied to assess the limitations of the water CEPN.2HCl (API) system targeting specifically the effect of initial polymorph composition. This is discussed below.

Figure 17A:
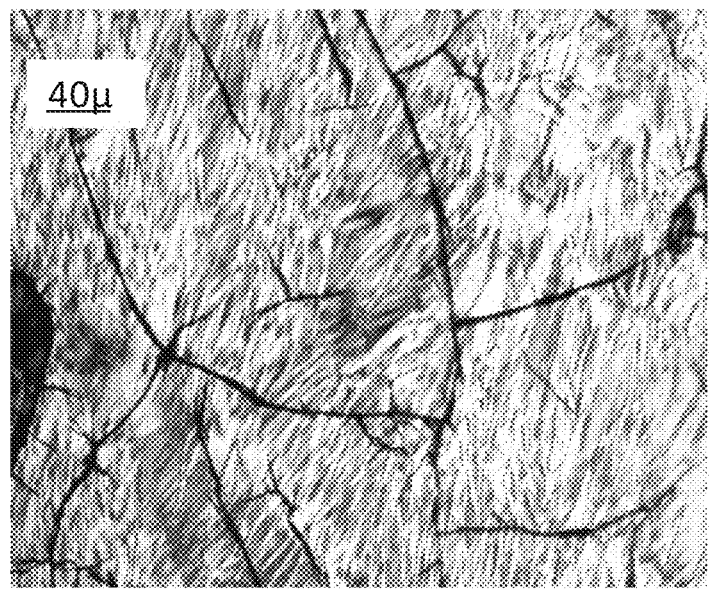
Figure 17B:
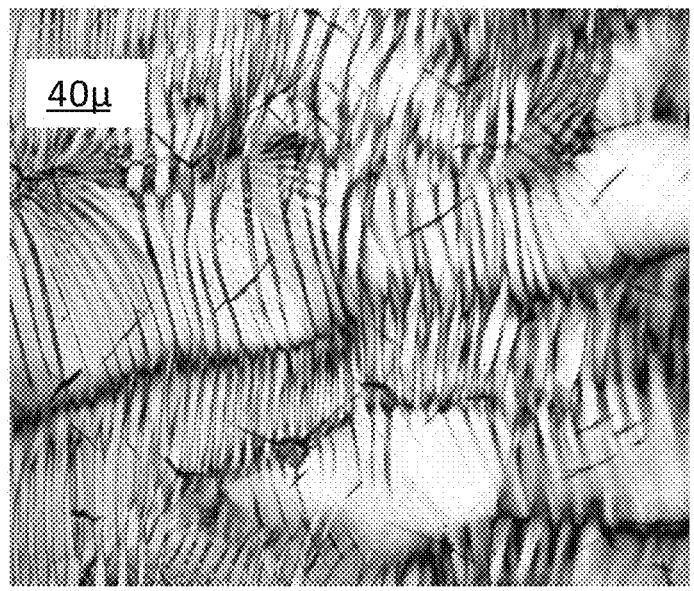
Figure 17C:
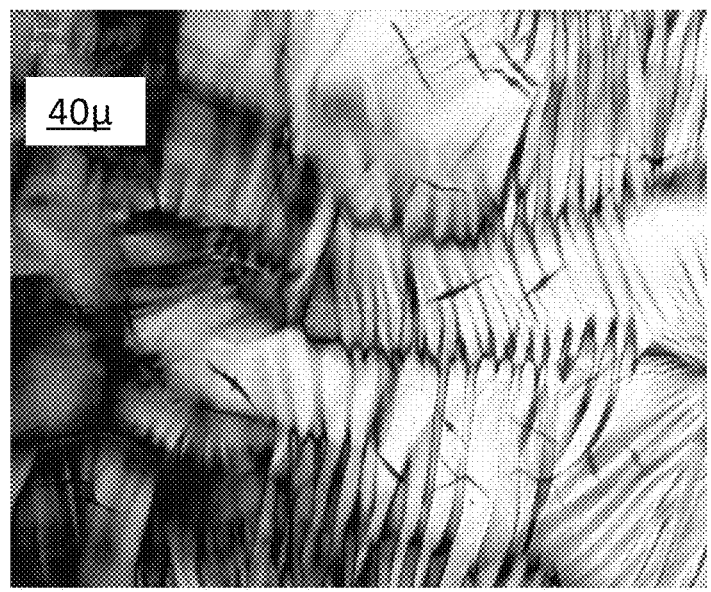
Figure 17D:
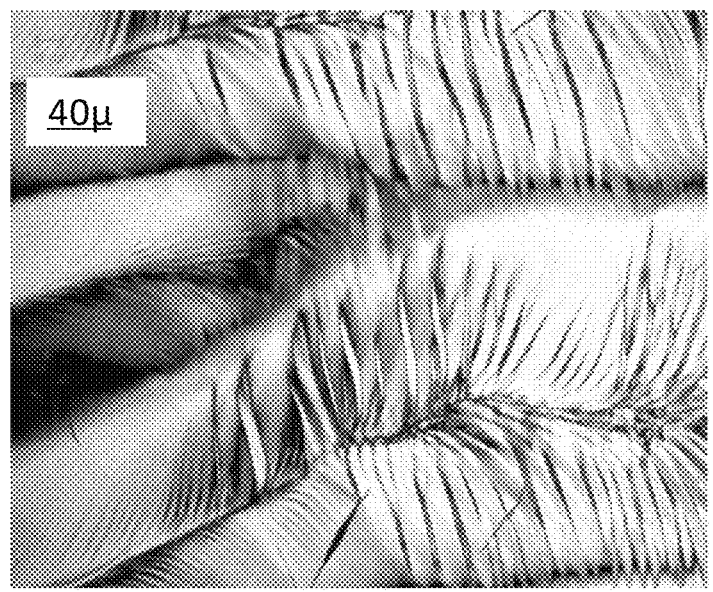

When 100 mg of the solid recrystallized CEPN.2HCl of varying polymorph compositions (four different samples)

was initially added to about 380 mg of deionized water, a paste resulted. When an additional 300 mg of deionized water was added and the mixture stirred overnight at RT, all four samples formed colorless, clear viscous liquids with trapped air bubbles. Under the polarized light microscope, all four samples showed domains and birefringence typical of liquid crystals as shown in FIG. 17A (sample 16-0203-012-097-27), FIG. 17B (sample 16-0203-012-098-27), FIG. 17C (sample 16-0203-012-098-10) and FIG. 17D (16-0203-012-105-23). Accordingly, in the broad context of the present invention, it has been recognized that one places a mixture of recrystallized polymorphs of CEPN 2HCl, into water, one can now prepare a liquid solution, which indicates birefringent (a refractive index that depends on the polarization and propagation direction of light) liquid crystallinity.

In some cases these solutions will form transparent gels reminiscent of the gels observed in the rat stomachs when initially transparent solutions were dosed. In this regard when a total of 1.8 ml deionized water (in 0.1 ml increments) had been added to each sample, all four samples turned slightly cloudy with very small amounts of solid visible. A small amount of the sample (0.6 ml) was removed from each vial and centrifuged to collect 0.3 ml clear supernatant. Within about 10-20 min, all four clear colorless liquid supernatants turned into gels. A stable saturated solution at room temperature was not reached until dilution to ca 3.9% w/w CEPN.2HCl. A portion of these saturated solutions containing a very small amount of suspended solid was filtered through 0.45 μm PTFE syringe filters and the filtrate samples were sent for HPLC analysis (Table 9). The impurity analysis by Mass Spectroscopy indicated that the unidentified impurity (one molecule) in Table 9 below was similar to CEPN and had been carried through the purification process from the original CEPN supply.

TABLE 9

HPLC Analysis Of Polymorph Composition

| Sample No. | Sample solubility (mg/ml) | Impurity peak area (%)* |
|---|---|---|
| 16-0203-012-097-27 | 31.9 | 0.37 |
| 16-0203-012-098-10 | 38.7 | 0.38 |
| 16-0203-012-098-27 | 39.7 | 0.35 |
| 16-0203-012-105-23 | 36.5 | 0.56 |

*relative retention time 0.653

As can therefore be seen from the above, the recrystallization protocol herein provides at least two or more polymorphs of CEPN.HCl having a purity of greater than or equal to 99.4%, with the remainder being an unidentified impurity. More preferably, it is contemplated that the purity of the at least two or more polymorphs present from the recrystallization protocol herein can be ≥99.5%, or > to 99.6%, or >99.7%, or ≥99.8%, or ≥99.9%. In addition, the recrystallization protocol herein is such that it readily provides the ability to prepare the recrystallized CEPN.HCl in amounts from 100 g up to 50 kg with the aforementioned purity.

A 100 mg of solid sample (5 kg engineering batch: CEPN-ENG-06-21-2016, 16-0203-012-119-35) containing predominantly polymorphs A and B (similar to the ca 8 kg cGMP sample) was mixed with 2.0 ml deionized water and the resulting viscous solution was magnetically stirred overnight at RT to produce a clear colorless solution with a very small amount of gel-like substance. After filtering through a 0.45 μm PTFE syringe filter; the clear colorless liquid filtrate turned into a clear gel. An additional 0.1 mL deionized water was added to the 0.3 g gelled filtrate sample, and the mixture was magnetically stirred overnight at RT to produce a mobile clear solution which did not gel. The sample was filtered through a 0.45 μm PTFE syringe filter and the filtrate sent for HPLC analysis (Table 10).

TABLE 10

HPLC of Mixed Polymorphs A and B Sample

| Sample No. | Sample solubility (mg/ml) | Impurity peak area (%)* |
|---|---|---|
| 16-0203-012-119-35 | 33.9 | 0.31 |

It may therefore be appreciated herein that relatively stable, non-gelling, one phase saturated solutions could be obtained from the polymorph distributions obtained herein by the described recrystallization protocol, preferably at RT (20-23° C.) in the range of ≤45 mg/ml. More preferably, the concentration may fall in the range of 20 mg/ml to 45 mg/ml, or even more preferably, in the range of 30 mg/ml to 40 mg/ml. It is also contemplated that this solubility will be maintained at 37° C. in water at the pH (slightly acid) determined by the concentration and $pK_a$ of the CEPN.2HCl; however, in vivo, protein complexation, ion concentrations and pH differences in the stomach and small intestine may affect this solubility. The conclusion is that it is problematic to dose concentrated aqueous solutions of CEPN.2HCl into the stomachs of animals because of the complicated phase behavior illustrated above which may affect downstream bioavailability and toxicity. More dilute solutions could possibly be used but this strategy would require large volumes of fluid which may be incompatible with dose volumes tolerated by the animals.

Example 5

Enteric Formulation Synthesis and Characterization

Figure 18:
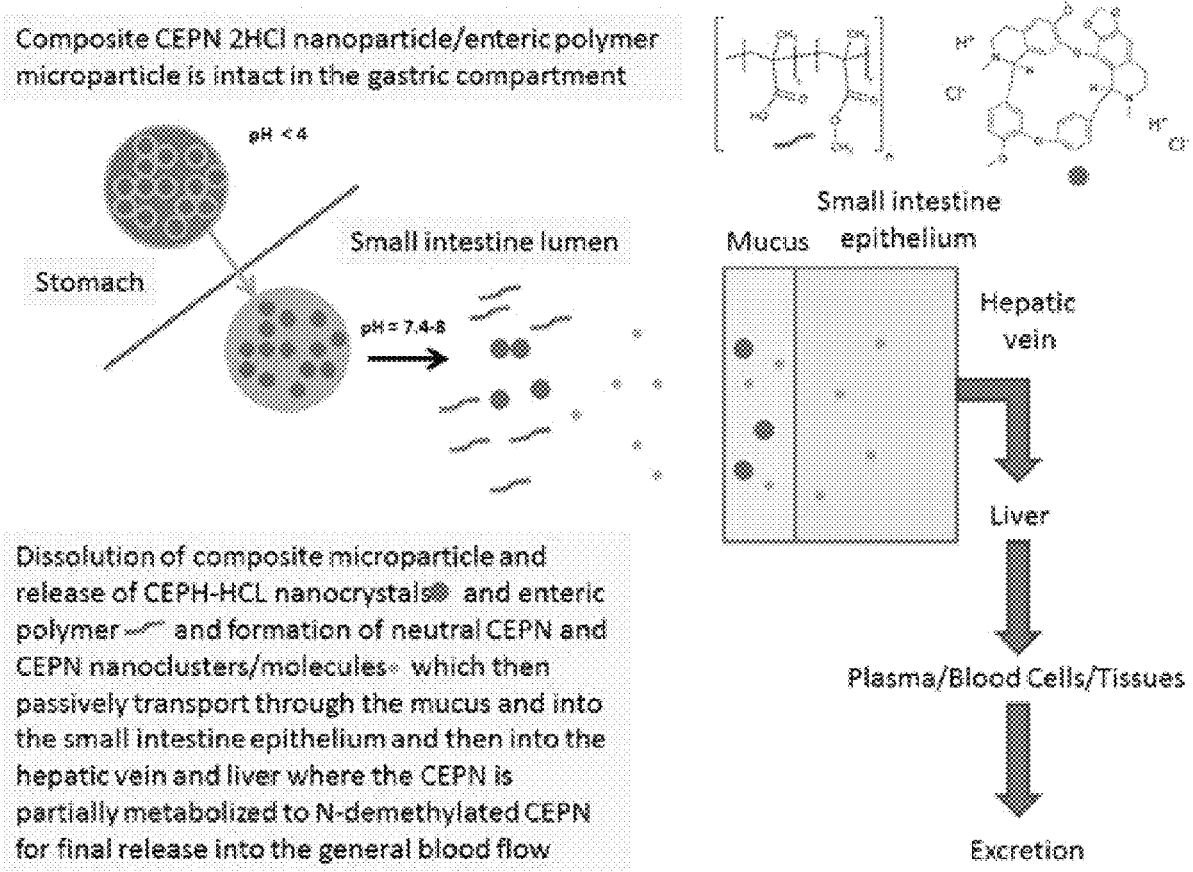

A procedure that produces a solid amorphous CEPN 2HCl enteric structure would be preferable since controlled release would not depend on an initial crystal polymorph distribution. The strategy herein for enteric formulations starting from the recrystallized polymorphic CEPN.2HCl material is shown in FIG. 18. In broad embodiment, the recrystallized mixture of at least two purified polymorphs of CEPN 2HCl forms a freely flowing liquid organic/aqueous phase that is now capable of being employed to form an enteric formulation that produces an amorphous mixture of CEPN.2HCl within a multimicron diameter API/excipient particle having a polymeric coating, which coating may preferably comprise, e.g., a methacrylic acid/methyl methacrylate copolymer. Other polymeric coatings contemplated include hydroxypropyl methyl cellulose phthalate (HPMCP), poly (vinyl acetate phthalate), cellulose acetate trimellitate (CAT), cellulose acetate phthalate (CAP) and shellac (esters of aleuritic acid).

An enteric formulation sample containing 25% w/w CEPN.2HCl (Lot ENG-CEPN-06212016), 5-kg pilot plant run after additional 3-day drying at 70° C. in 75% w/w Eudragit L100 (1/1:methacrylic acid/methyl methacrylate enteric copolymer) was prepared by a spray drying process. L100 is protonated and insoluble at pH 1-5 and starts deprotonating and swelling at pH >6. This formulation can be placed into gel caps or gavaged as a water suspension.

Reference to enteric formulation may be understood herein as placement of the amorphous mixture of CEPN.2HCl within a polymeric barrier that minimizes (≤20% release) or prevents dissolution or disintegration in the gastric environment.

Oral Dosing

Figure 19:
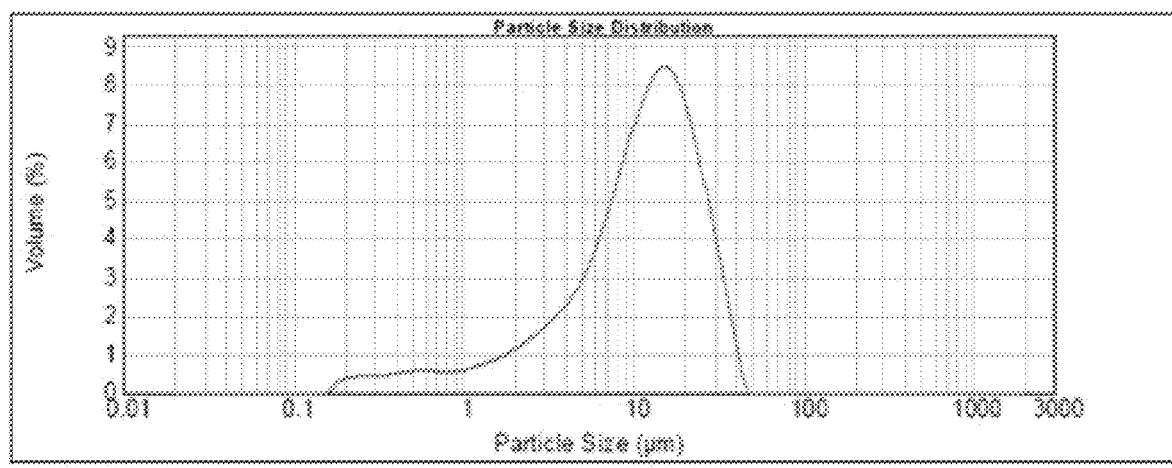
Figure 20A:
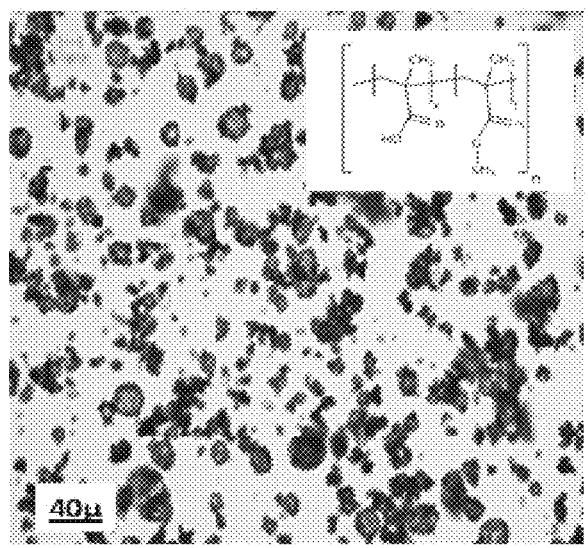
Figure 20B:
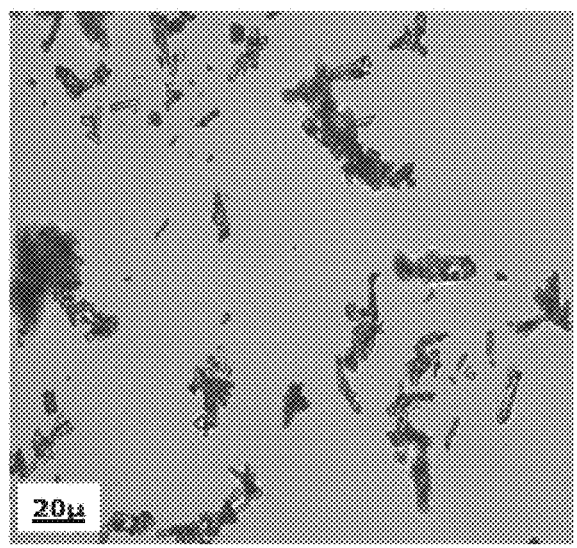

Preferably, to form the enteric formulation both L100 and the recrystallized mixture of two or more polymorphs of CEPN.2HCl are introduced into a mixture of water soluble organic solvents with water, wherein the water soluble organic solvents are present at a level of >85% by weight, more preferably ≥90% by weight, or even more preferably >95% by weight. For example, acetone (38%) and 2-propanol (57%) with water (5% by weight). The slightly hazy liquid mobile phase (meaning liquid containing the recrystallized mixture of two or more polymorphs of CEPN-HCl and polymer for enteric coating) was spray dried with inlet temperature preferably set to evaporate the solvents, e.g. set around 80° C. which resulted in white free-flowing powder (sample 16-0202-014-p50) with average particle size of about 13 μm. The preferred average particle size herein is contemplated to therefore fall in the range of 10 μm to 20 μm. See FIG. 19. FIG. 20A is a polarized optical microscope image of the enteric formulation and FIG. 20B is the polarized optical microscope image of CEPN 2HCl crystals showing needle/plate like crystals (A, B, D polymorph mixture) prior to spray drying.

Figure 21A:
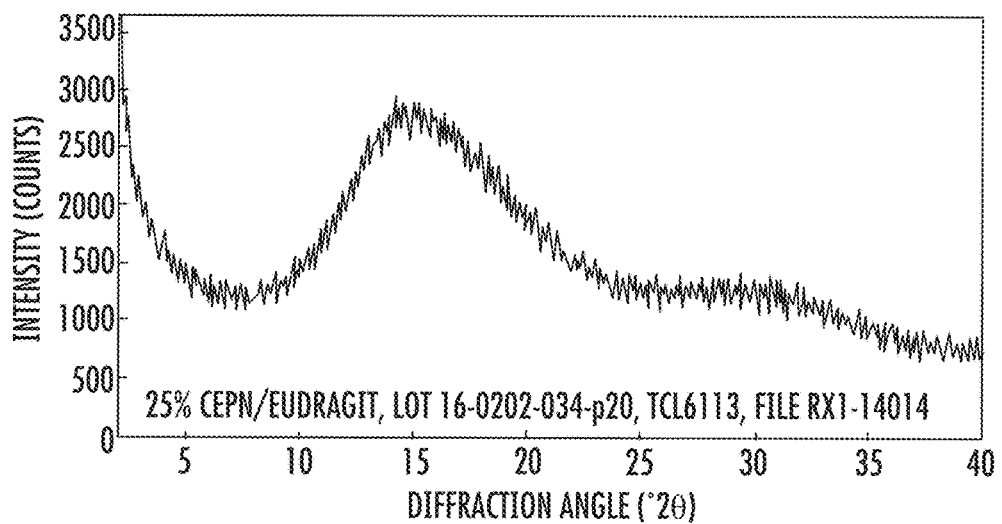
Figure 21B:
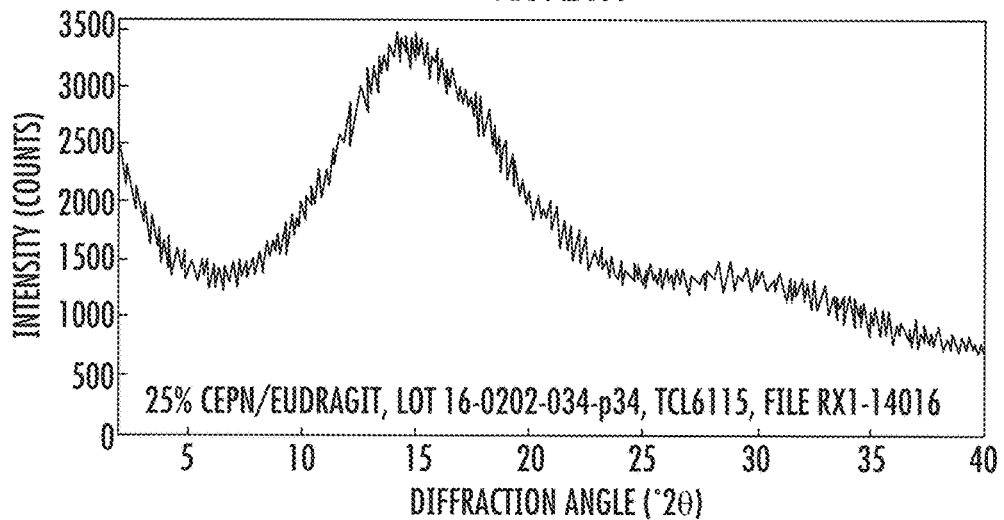
Figure 21C:
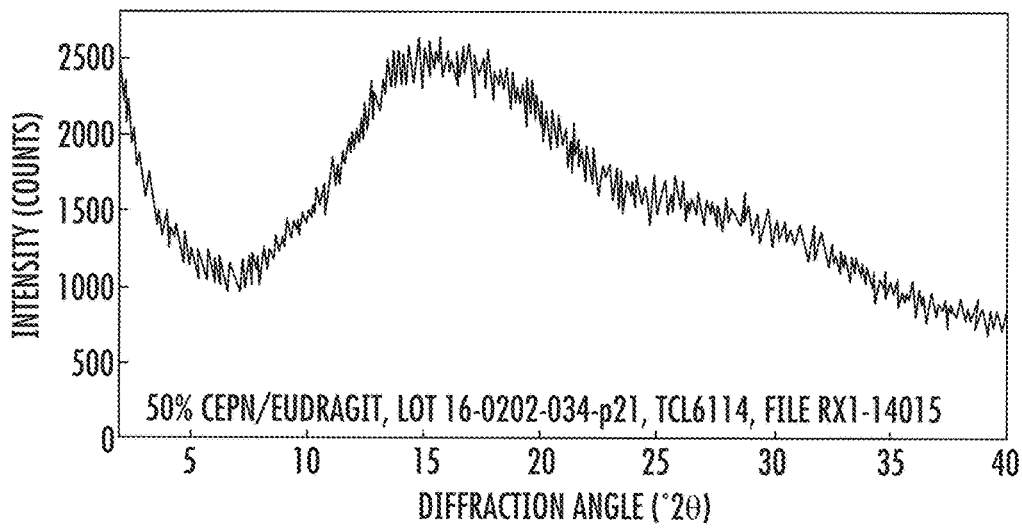

It should be noted that bright, somewhat colored, phase separated inclusions are seen in the larger particles in FIG. 20A suggests either crystalline or amorphous liquid crystalline structures. FIG. 21 shows the amorphous X-ray diffraction patterns of three enteric formulations formed from the recrystallized polymorphic mixtures herein containing either 25% or 50% (w/w) of CEPN.2HCl in L100. That is, it can be understood that amorphous liquid crystal form of Cepharanthine-2HCl is such that the X-rays scatter in multiple directions without any relatively high intensity peaks at select values of 2θ. For example, a scattering pattern comprising a relatively broad first peak distributed over a relative wide 2θ range of 10° to 20°, or as shown in FIG. 21, from about 7° to about 22°. A relatively weak and broad secondary peak can be seen at the 2θ range of 25° to 35°. Photography under crossed polarizers indicates that the inclusions are highly birefringent and suggests that they are amorphous liquid crystal inclusions of CEPN.2HCl embedded in the enteric matrix polymer. As noted above, FIGS. 17A, 17B, 17C and 17D suggested that CEPN.2HCl would have a tendency to form amorphous liquid crystals under certain conditions. The amorphous structure suggests that the enteric compositions would be able to deliver supersaturated solutions of the CEPN API to the small intestine thus increasing bioavailability. Accordingly, in the broad context of the present invention, the recrystallization protocol herein allows for a method of treating an individual infected with filovirus with an enteric formulation that includes a polymeric barrier and an active pharmaceutical ingredient that comprises, consists essentially of, or consists of an amorphous liquid crystalline form of Cepharanthine.2HCl.

Elemental analysis of both the ENG and cGMP batches shows a chlorine/nitrogen (w/w) ratio 2.5 or molar ratio of 1:1-indicative of the dihydrochloride salt. The 25% and 50% (w/w) CEPN.2HCl in the spray dried L100 formulation also show a 2.5 (w/w) ratio (within experimental error) indicating that the CEPN.2HCl stoichiometry within the enteric composite particle is maintained after spray drying (Table 11).

TABLE 11

Elemental Analysis

| Sample Detail | Cl/N weight ratio |
|---|---|
| API only cGMP | 2.53 |
| API only ENG | 2.49 |
| L 100 Eudragit polymer | No halogen or nitrogen detected |
| 25% (w/w) cGMP API in L100 | 2.64 |
| 25% (w/w) ENG API in L 100 | 2.58 |
| 50% (w/w) ENG API in L 100 | 2.54 |

Details of Enteric Preparation

L-100 Microsphere Enteric Preparation

Prepared a solvent mixture of 2-propanol (1530±15 g), acetone (1020±9 g), and water (120±3 g)

Dissolved Eudragit L100 (123±1 g) in the above solvent mixture under magnetic stirring. Following TAP 01-0202-067 "Operation of the Pro-C-epT 4M8 Spray Dryer", the resulting solution was spray dried using a 0.6 mm nozzle with an inlet air temperature of 80° C. and 103 g of sample was collected.

The above steps (1-3) were repeated and stopped when 57 g of sample was collected.

The two samples were combined and vacuum dried until constant weight. A total of 150 g of sample was collected after vacuum drying (Sample 17-0202-009-p32).

The process yield was 84%

CEPN.2HCl/L-100 Microsphere Enteric Preparation

Prepared a solvent mixture of 2-propanol (3570±35 g), acetone (2380±21 g), and water (280±7 g).

Dissolved Eudragit L100 (287±1 g) in the above solvent mixture under magnetic stirring.

Dissolved recrystallized CEPN.2HCl (98±1 g) containing at least two or more polymorphs (Scheme 1) in the above polymer solution.

Following TAP 01-0202-067 "Operation of the Pro-C-epT 4M8 Spray Dryer", the resulting solution was spray dried using a 0.6 mm nozzle with an inlet air temperature of 80° C. and 333 g of sample was collected.

The above steps were repeated multiple times and stopped when a total of approximately 2.5 kg sample was obtained.

Approximately half of the samples were combined and vacuum dried until constant weight. The remaining half was vacuum dried later until constant weight. The two drying processes were conducted sequentially so that a sample could be shipped in time for a nonclinical study.

A total of 2455 g of sample was collected after vacuum drying (1015 g of Sample 17-0202-009-p6 and 1440 g of Sample 17-0202-009-p26).

The process yield was 86%.

Sample Package

The vacuum dried samples were combined in a large polypropylene (PP) plastic bucket and shaken to mix.

The samples were stored in labeled PP plastic jars at controlled ambient temperature.

Example 6. Enteric Formulation In Vitro Controlled Release

An in vitro release study was conducted with the 25% CEPN.2HCl in L100 enteric sample. Specifically about 80 mg sample was placed in 10 ml simulated-gastric-fluid without pepsin and gently stirred at 37° C.; samples were collected at t=0, 1 and 2 hrs. Another 80 mg sample was then placed in 20 ml simulated-intestinal-fluid without pancreatin and gently stirred at 37° C. and collected at t=0, 1, 2, 3 and 23 hrs. 20% of drug in the sample was released in the simulated gastric fluid after two hours, which is much longer than a typical retention time in the stomach and suggests that the formulation would enter the small intestine relatively intact.

In the simulated intestinal fluid, the formulation particles rapidly swelled and released API which precipitated over time, most probably as growing, unprotonated, free base CEPN crystals to form a cloudy suspension either within the swollen particles or in the solution between particles. In vivo the amount of neutral CEPN passing through the small intestinal wall and into the liver through the hepatic portal vein would depend upon several factors including small intestine transit time, particle size, protein complexation, proximity to the mucous layer coating the interior of the small intestines.

Example 7

Pharmacokinetic (PK) Studies of 25% CEPN.2HCl Enteric Formulation Suspension-5 Day Dosing Study in Rats The principal objective of this study was to determine an oral dosing schedule that would provide high enough blood plasma concentrations that would be effective as prophylaxis/therapy against filo and other viruses in infected animals and ultimately humans. In the PK phase of this study, male and female animals were dosed by oral gavage once a day for 5 days (days 0, 1, 2, 3, 4) at 50, 150, and 300 mg/kg CEPN.2HCl using a spray dried enteric formulation which consisted of Eudragit L100 polymer and 25% (w/w) CEPN.2HCl. All three suspensions were well tolerated in the animals. Clinical observations were taken daily and body weight was obtained twice per week. Blood samples were collected at multiple time points to determine a plasma PK profile by LC/MS/MS (liquid chromatography/mass spectrometry/mass spectrometry).

PK results demonstrate a non-linear dose proportionality of CEPN. FIGS. 22 A, B and C illustrate CEPN rat plasma concentration for oral (gavage) enteric doses (25% w/w CEPN 2HCl in L100) of 50 mg/kg, 150 mg/kg, 300 mg/kg (rat weight) respectively, API. The plasma levels reached a $C_{max}$ of 1400 ng/mL which is in the range for effective antiviral activity, The rats had a marked accumulation of CEPN in the plasma over 5 days of daily dosing, ranging from 2.2- to 6.7-fold for $C_{max}$ and 3.4 to 7-fold for AUC when compared to Study Day 0 levels (Table 7-non-compartmental model). Evaluating the data using one and two compartmental models did not lead to any additional insights. A longer terminal, elimination half life for multiple dosing when compared to a single dose indicates a desirable bioaccumulation in plasma and undoubtedly other organs. After the fifth dose, half of the animals were euthanized and a gross necropsy was performed.

Microscopic examination of the liver from the 300 mg/kg/day animals showed vacuolization of the cytoplasm (non-adverse). In addition the livers were slightly enlarged compared to the mid (150 mg/kg/day) or low (50 mg/kg/day) groups, which could be one underlying cause of the initial plasma depletion. Of course accumulation in the liver is desirable since it is the primary site of viral multiplication after migration of the virus from circulatory/or lymph system. As CEPN will be used for a life-threatening disease and there were no test article-related deaths, the highest dosage level evaluated, 300 mg/kg/day, is considered tolerable in the scope of this phase (Pharmacokinetic Study) following 5 consecutive days of dosing. This dosage level corresponds to a final $C_{max}$ of 1.4 µg/mL and a final AUC 0→∞=70 µg/mL*h which is close to that calculated for in vitro determined effectiveness against filovirus infected primary macrophages circulating in the plasma.

Accordingly, the present disclosure is directed at supplying Cepharanthine which is formed into a dihydrochloride salt followed by recrystallization into a mixture of at least two polymorphs at relatively high purity which can be introduced into an organic/aqueous solvent mix to form a mobile liquid that can be spray dried into an enteric formulation containing an amorphous mixture of CEPN 2HCl. The enteric formulation may then be relied upon to provide for much more efficient dosage regimes for treatment of viral infections, via routes of administration including water suspension gavage solution dosing or inclusion into gel caps that can be more effectively utilized for human dosing.

What is claimed is:

1. A method of forming an enteric formulation of Cepharanthine.2HCl comprising:
    (a) providing Cepharanthine and dissolving in ethyl acetate containing hydrochloric acid and forming the dihydrochloride salt of Cepharanthine comprising Cepharanthine.2HCl of the following formula:

(b) recrystallizing said Cepharanthine.2HCl salt from an ethanol-water solution and forming a mixture of at least two polymorphs at a purity of ≥99.4% wherein said polymorphs indicate a distinct x-ray diffraction peak at 2Θ angles of 5.5 or 8.9;

(c) introducing said recrystallized Cepharanthine.2HCl in combination with a polymer into a mixture of a water soluble organic solvent containing water to provide a liquid mobile phase;

(d) forming a solid enteric formulation from said liquid mobile phase to produce an enteric particle containing an amorphous liquid crystal form of said Cepharanthine.2HCl salt wherein said amorphous liquid crystal form indicates an amorphous x-ray diffraction pattern comprising a first peak distributed over a 2Θ range of 7° to 22° and a second peak distributed over a 2Θ range of 25° to 35°.

2. The method of claim 1 wherein recrystallizing said Cepharanthine.2HCl salt comprises dissolving Cepharanthine.2HCl in an ethanol/water mixture comprising 80-99 parts ethanol and 1-20 parts water and recovering recrystallized Cepharanthine.2HCl.

3. The method of claim 1 wherein said enteric formulation has a particle size distribution in the range of 10 μm to 20 μm.

4. The method of claim 1 wherein said water soluble organic solvent/water mixture comprises water soluble organic solvent at a level of ≥85% by weight.

5. The method of claim 1 wherein said polymer comprises methacrylic acid/methyl methacrylate copolymer.

6. A method of forming an enteric formulation of Cepharanthine.2HCl comprising:

(a) providing Cepharanthine and dissolving in ethyl acetate containing hydrochloric acid and forming the dihydrochloride salt of Cepharanthine comprising Cepharanthine.2HCl of the following formula:

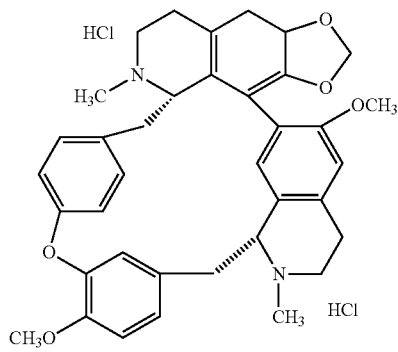

(b) recrystallizing said Cepharanthine.2HCl salt from an ethanol-water solution comprising 80-99 parts ethanol and 1-20 parts water and recovering recrystallized Cepharanthine.2HCl salt comprising mixture of at least two polymorphs at a purity of ≥99.4% wherein said polymorphs indicate a distinct x-ray diffraction peak at 2Θ angles of 5.5 or 8.9;

(c) introducing said recrystallized Cepharanthine.2HCl in combination with a polymer into a mixture of a water soluble organic solvent/water mixture comprising water soluble organic solvent at a level of ≥85% by weight, to provide a liquid mobile phase, wherein said water soluble organic solvent is selected from acetone or propanol;

(d) forming a solid enteric formulation from said liquid mobile phase to produce an enteric particle containing an amorphous liquid crystal form of said Cepharanthine.2HCl salt at a particle size of 10 μm to 20 μm wherein said amorphous liquid crystal form indicates an amorphous x-ray diffraction pattern comprising a first peak distributed over a 2Θ range of 7° to 22° and a second peak distributed over a 2Θ range of 25° 35°.

* * * * *